(12) United States Patent
Miller et al.

(10) Patent No.: US 7,312,080 B2
(45) Date of Patent: Dec. 25, 2007

(54) PLANT RESISTANCE TO INSECT PESTS MEDIATED BY VIRAL PROTEINS

(75) Inventors: W. Allen Miller, Ames, IA (US); Bryony C. Bonning, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 611 days.

(21) Appl. No.: 10/346,144

(22) Filed: Jan. 15, 2003

(65) Prior Publication Data

US 2003/0217385 A1 Nov. 20, 2003

Related U.S. Application Data

(63) Continuation of application No. 09/395,401, filed on Sep. 14, 1999, now abandoned.

(60) Provisional application No. 60/100,132, filed on Sep. 14, 1998.

(51) Int. Cl.
*C12N 5/00* (2006.01)
*C12N 15/63* (2006.01)
*C12P 21/06* (2006.01)
*A61K 38/00* (2006.01)
*C07H 21/04* (2006.01)

(52) U.S. Cl. .................. 435/375; 435/6; 435/69.1; 435/71.3; 435/91.1; 435/455; 530/300; 530/326; 536/23.4; 536/23.5; 536/23.72

(58) Field of Classification Search .............. 530/300, 530/350, 324, 370, 326; 435/6, 69.1, 71.3, 435/91.1, 455, 375; 536/23.1, 23.4, 23.72, 536/23.5
See application file for complete search history.

(56) References Cited

U.S. PATENT DOCUMENTS

| 5,143,905 | A | | 9/1992 | Sivasubramanian et al. .. 514/21 |
| 5,306,628 | A | * | 4/1994 | Sivasubramanian et al. ..... 435/69.7 |
| 5,618,699 | A | | 4/1997 | Hamamoto et al. ........ 435/69.7 |
| 5,770,192 | A | | 6/1998 | Cayley et al. ............. 424/93.2 |
| 6,077,992 | A | | 6/2000 | Yadav ....................... 800/278 |
| 6,689,356 | B1 | * | 2/2004 | Zlotkin et al. ............. 424/93.2 |

FOREIGN PATENT DOCUMENTS

| EP | 0 608 696 A2 | 3/1994 |
| WO | 94/19477 | 1/1994 |

OTHER PUBLICATIONS

Miller, W.A. et al., Virology, vol. 165, pp. 306-309 (1988).*
Chay, C.A. et al., Virology, vol. 219, pp. 57-65 (1996).*
Tian, T. et al., Virology, vol. 231, pp. 204-212 (1995).*
Brault, J. et al. "Aphid Transmission of Beet Western Yellows Luteovirus Requires the Minor Capsid Read-through Protein P74;" (1995) *EMBO J.* 14:650-659.
Brown,C.M. et al. "Local and Distant Sequences Are Required for Efficient Readthrough of the Barley Yellow Dwarf Virus PAV coat Protein Gene Stop Codon;" (1996) *J. Virol.* 70:5884-5892.
Chay, C.A. et al. "Aphid Transmission and Systemic Plant Infection Determinants of Barley Yellow dwarf Luteovirus-PAV are Contained in the Coat Protein Readthrough Domain and 17-kDa Protein, Respectively;" (1996) *Virology* 219:57-65.
DeDianous, S. et al. "Re-Examination of the Specificity of the Scorpion *Androctonus australis* Hector Insect Toxin Towards Arthropods;" (1987) *Toxicon* 25:411-417.
Filichkin, S.A. et al. "In Vivo Expression and Mutational Analysis of the Barley Yellow Dwarf Virus Readthrough Gene;" (1994) *Virology* 205:290-299.
Gershburg, E. et al. "Baculovirus-mediated Expression of a Scorpion Depressant Toxin Improves the Insecticidal Efficacy Achieved with Excitatory Toxins;" (1998) *FEBS Lett.* 422:132-136.
Gildow, F.E. et al. "The Aphid Salivary Gland Basal Lamina as a Selective Barrier Associated with Vector-Specific Transmission of Barley Yellow Dwarf Luteoviruses;" (1993) *Phytopathology* 83:1293-1302.
Gray, S.M. "Plant Virus Proteins Involved in Natural Vector Transmission;" (1996) *Trends in Microbiol.* 4:259-264.
Herrmann, R. et al. "The Tolerance of Lepidopterous Larvae to an Insect Selective Neurotoxin;" (1990) *Insect Biochemistry* 20:625.
Kammann, M. et al., "DNA Replication of Wheat Dwarf Virus, A Geminivirus, Requires Two cis-Acting Signals;"(1991) *Virology* 184(2):786-90.
Maeda, S. et al. "Insecticidal Effects of an Insect-Specific Neurotoxin Expressed by a Recombinant Baculovirus;" (1991) *Virology* 184:777-780.
McCutchen, B.F. et al. "Development of a Recombinant Baculovirus Expressing an Insect-selective Neurotoxin; Potential for Pest Control"; (1991) *Bio/Technol.* 91:848-852.
Miller, W.A. et al. "Are there Risks Associated with Transgenic Resistance to Luteoviruses?;" 1997 *Plant Disease* 81:700-710.

(Continued)

*Primary Examiner*—Jane Zara
(74) *Attorney, Agent, or Firm*—Greenlee, Winner and Sullivan, P.C.

(57) ABSTRACT

The invention involves combining a peptide toxin effective against insects, including but not limited to thrips, leaf hoppers, and beetles, with a transport peptide capable of facilitating transfer of the peptide toxin from the gut of an insect to the hemocoel. The combination can be effected by a fusion of genetic material encoding the peptide toxin and the transport peptide, such that expression of the genetic material fusion results in synthesis of a fusion protein combining the functions of both the toxin and the transport protein. Ingestion of the fusion protein by the sucking insect transfers the fusion protein into the insect's gut from which it is transferred into the hemocoel due to the functional activity of the transport peptide where the toxin exerts its toxic effect upon the insect. In a preferred embodiment, the invention is effective in control of such sucking insects as aphids, whiteflies and the like, and other vectors that transmit viruses in a circulative manner.

16 Claims, 6 Drawing Sheets

OTHER PUBLICATIONS

Miller, W.A. et al. Sequence and Organization of Barley Yellow Dwarf Virus Genomic RNA, (1988) *Nucleic Acids Research*, 16(13):6097-6111.

Power, A.G. et al. *Barley Yellow Dwarf: 40 Years of Progress* (1995) St.Paul: APS Press, pp. 259-289, (Figs. 1 and 2).

Rizzo, T.M. et al. Localization of a Surface Domain of the Capsid Protein of Barley Yellow Dwarf Virus (1992) *Virology* 186:300-302.

Stewart, L.M.D. et al. "Construction of an Improved Baculovirus Insecticide Containing an Insect-Specific Toxin Gene;" (1991) *Nature* 352:85-88.

Van den Heuvel, J.F.J.M. et al. "The N-Terminal Region of the Luteovirus Readthrough Domain Determines Virus Binding to *Buchnera* GroEL and its Essential for Virus Persistence in the Aphid;" (1997) *J. Virol.* 71:7528-7265.

Zlotkin, E., *Neuropharmacology and Pesticide Action,* (1986) Ellis Horwood Ltd., Chichester, England (publ.) pp. 352-383.

* cited by examiner

PLANT RESISTANCE TO INSECT PESTS MEDIATED BY VIRAL PROTEINS

CROSS REFERENCE TO RELATED APPLICATIONS

This application is a continuation application of U.S. application Ser. No. 09/395,401 filed Sep. 14, 1999 now abandoned, which claims priority from U.S. Provisional Application No. 60/100,132 filed Sep. 14, 1998.

ACKNOWLEDGMENT OF FEDERAL RESEARCH SUPPORT

This invention was made, at least in part, with funding from the United States Department of Agriculture under contract No. 97-34340-3987. Accordingly, the U.S. government may have certain rights in this invention.

BACKGROUND OF THE INVENTION

Most plant viruses are transmitted by insect vectors. Others are transmitted by mites, fungi or nematodes. Viruses that infect insects, such as baculoviruses, also enter the hemocoel of the insect from the gut through the action of virus coat proteins. Circulatively transmitted plant viruses enter the hemocoel (body cavity) of the insect vector. Viruses that infect insects also enter the hemocoel. In all cases, they have evolved specialized proteins to ensure their survival in the vector. This invention intends to exploit these viral proteins, and the genes encoding them, for presentation and delivery of toxins or other proteins to the vector or related organism. This may apply to non-vectors as well as vectors because, in some cases, viruses often interact with and enter the hemocoel of non-vectors. Furthermore, the viral proteins can be modified to interact with a wider range of organisms than occurs in nature. By facilitating efficient delivery of toxins, this invention can be used to genetically engineer pest-resistant plants, or to construct biopesticides.

Plant viruses can be transmitted in a circulative or non-circulative fashion. We define circulative transmission broadly as "any plant virus that must be actively transported across vector membranes and survive inside the vector to be transmitted" (Gray, S. M. [1996] *Trends in Microbiology* 4:259-264). By this definition, even some fungi can be considered circulatively transmitting vectors. In general, viruses are understood in the art as classifiable within groups which share common features of genetics, structure and the like. Examples of virus groups that are transported across insect vector membranes include: tospoviruses, plant reoviruses, plant rhabdoviruses, tenuiviruses, marafiviruses, luteoviruses, geminiviruses, enamoviruses, tymoviruses, comoviruses, and sobemoviruses (ibid: Gergerich, R. C. and Scott, H. A. [1991] *Advances in Disease Vector Research*. Harris, K. F., ed., pp. 114, Springer-Verlag). The fungally transmitted viruses include bymoviruses and furoviruses (op cit.; Jianping et al. [1991] *Annals of Applied Biology* 118: 615-622). This invention encompasses all such viruses and their vectors and non-vectors which can acquire the virus.

The term "luteovirus" is used herein to encompass all viruses of the family Luteoviridae, including three major genera: *Luteovirus, Polerovirus* and *Enamovirus*. The RPV strain of Barley yellow dwarf virus (BYDV) described in examples herein, is also termed "cereal yellow dwarf virus—RPV" and classified in the genera Polerovirus, as the result of a recent change in nomenclature. However, since the majority of relevant art refers to BYDV, that nomenclature is retained herein.

Noncirculatively transmitted viruses "associate with the cuticular lining of the insect mouthparts or foregut and are released as the insect expels digestive secretions into the plant when it begins to feed. These viruses are not actively transported across vector-cell membranes, nor are they carried internally. The external cuticular lining of insects (and nematodes) extends well into the mouthparts and foregut, but is shed when the animal molts." (Gray, S. M. [1996] *Trends in Microbiology* 4:259-264). Although the application herein exemplifies the use of plant virus proteins to deliver toxins to the hemocoel, noncirculatively transmitted viruses may be used similarly to present toxins to the surfaces of the gut or mouthparts. In principle, any virus which can enter the hemocoel of an insect from the gut through the action of viral protein can be employed, as described, to deliver a toxin to the insect.

The invention is exemplified herein by luteoviruses and their aphid vectors. They have the best-characterized circulatively-transmitted virus-vector interactions. However, the same principles can be applied for any virus-vector interaction and their exploitation to develop insect-resistant plants is included in this invention.

Luteoviruses can be transmitted only by aphids. The transmission mechanism is persistent and circulative. The virus enters the body cavity (hemocoel) of the aphid where it can remain for the life of the aphid. The aphid acquires virus by feeding on an infected plant. The virus particles (virions) are transported from the aphid hindgut into the hemocoel by a presumed receptor-mediated process across the hindgut epithelial cells. From the hemocoel, the virus is then transported across two more membrane barriers into the accessory salivary gland (ASG) (Gildow, F. E. et al. [1993] *Phytopathology* 83:1293-1302; Power, A. G. et al. [1995] in *Barley Yellow Dwarf: 40 Years of Progress*, St. Paul: APS Press, pp. 259-289), (FIGS. 1, 2). Subsequently, each time the aphid feeds, it transmits virus by secreting virus-laden saliva into the plant cells.

There is a high degree of vector specificity for different strains of luteoviruses (Power, A. G. et al. [1995] supra). However, many luteoviruses are transported across the hindgut membrane into the hemocoel, in many nonvector aphid species, (Gildow, F. E. et al. [1993] supra). Hence, vector specificity is thought to be enforced at the ASG barrier. Other viruses. such as potato leafroll virus, are transmitted across the midgut membrane. Nonluteoviruses are digested or excreted without uptake into the hemocoel. Thus, the hindgut epithelial receptors seem to be specific for luteoviruses (FIG. 2). This fact is exploited in the present invention.

The genome of luteoviruses consists of a single, positive sense, 5.7 kb RNA. The proteins needed for virus particles, aphid transmission, and virus movement within the plant all are expressed from a subgenomic RNA (sgRNA1) that is generated during virus infection but is not encapsidated in the virion (FIG. 3) (Miller, W. A. et al. [1997] *Plant Disease* 81:700-710). The luteovirus virion contains 180 copies of the coat protein (CP). About 5-10% of the CP subunits contain a long carboxy-terminal extension that protrudes from the virion (Filichkin, S .A. et al. [1994] *Virology* 205:290-299). This extension arises when ribosomes read through the stop codon of the CP open reading frame (ORF) during translation of sgRNA1 (FIG. 3), allowing translation of the downstream ORF5, resulting in a fused CP-readthrough domain (RTD) product (Brown, C. M. et al. [1996] *J. Virol.* 70:5884-5892).

The middle of the RTD (around amino acid 242) contains a labile peptide bond causing the C-terminal half to be cleaved in purified virus preparations (Filichkin et al. [1994]

supra). Because purified virions are readily aphid transmitted, the C-terminal portion is unnecessary for aphid transmission. On the other hand, the N-terminal half of the RTD is required for aphid transmission (from aphid to plant) (Brault, J. et al. [1995] EMBO J. 14:650-659; van den Heuvel, J. F. J. M. et al. [1997] J. Virol. 71:7258-7265), but not for virion assembly or transport across the hindgut membrane into the hemocoel (Chay, C. A. et al. [1996] Virology 219:57-65).

The major CP itself is also required for transmission because intact virions are necessary to protect the viral RNA. In the hemocoel, the N-terminal half of RTD is bound by an abundant protein called symbionin which is produced by endosymbiotic bacteria (van den Heuvel et al. [1997] supra; Filichkin, S. A. et al. [1997] J. Virol. 71:569-579). This protein strongly resembles bacterial chaperonin groEL which ensures correct folding of many different proteins. However, the binding by symbionin does not resemble that of groEL with its substrate proteins (Hogenhout, S. A. et al. [1998] J. Virol. 72:348-365). The ability of symbionin to bind the luteovirus virion correlates with increased half-life of the virion in the hemolymph (van den Heuvel et al. [1997] supra).

It has been found that a sequence just 3' of the CP ORF stop codon (proximal RT element) and a sequence located, surprisingly, 700-750 bases further downstream (distal RT element) are necessary for readthrough of the CP ORF stop codon during translation of sgRNA1 (Brown, C. M. et al. [1996] supra) (FIG. 3). The distal RT element still facilitates readthrough even after insertion of a reporter gene between it and the proximal element, causing the distal RT element to be located in the 3' untranslated region (UTR) 2 kb downstream from the CP stop codon (Brown, C. M. et al. [1996] supra).

Current aphid control relies heavily on the use of chemical insecticides. Insecticide application to control transmission of viruses by aphids can have the unintended opposite effect of increasing virus spread by increasing plant-to-plant movement of aphids agitated by sublethal doses, and by killing aphid predators (Schepers, A. [1989] in Aphids: Their Biology, Natural Enemies and Control, Minks, A. D. et al. [eds.], Elsevier, Amsterdam, Vol C, pp. 123-139). Moreover, the efficacy of chemicals against aphids is limited because of the rapid evolution of insecticide-resistant aphids. Alternative, environmentally benign means of aphid control are required to maintain agricultural productivity.

Use of aphid-resistant crop cultivars has been effective for limiting aphid damage (Auclair, J. L. [1989] in Minks et al., supra, pp. 225-265; Thackray, D. J. et al. [1900] Ann. Appl. Biol. 116:573-582). Aphid-resistant maize lines (Walter, E. V. et al. [1946] J Am. Soc. Agron. 38:974-977) and wheat lines resistant to the Russian wheat aphid (Diuraphis noxia) (Quisenberry, S. S. et al. [1994] J. Econ. Entomol. 87:1761-1768) have been developed by conventional plant breeding techniques. Transgenic plants that resist insects have been constructed with agents that are active in the gut of insects. The most notable example is the use of the Bacillus thuringiensis toxin (Bt) genes, but no Bt toxin is known that affects aphids. Transgenic tobacco engineered to express a lectin was shown to confer protection against aphids (Hilder, V. A. et al. [1995] Transgenic Res. 4:18-25), and numerous transgenic plants have been produced that resist aphid-transmitted viruses by the use of virus-derived transgenes (Miller, W. A. et al. [1997] supra; Anon [1995] Genetic Engineering News 15:1; Wilson, T. M. A. [1993] Proc. Natl. Acad. Sci. 90:3134-3141).

A second approach toward insect pest control has been the use of baculoviruses, which are insect specific viruses. Some of these viruses have been used to deliver a variety of insect-specific toxins that, are active in the hemocoel but not in the gut of the insect. For example, recombinant baculoviruses have been developed for control of lepidopteran (moth) pest species (Bonning, B. C. et al. [1996] Annu. Rev. Entomol. 41:191-210). These baculoviruses have been engineered to produce insect hormones such as diuretic hormone (Maeda, S. [1989] Biochem. Biophys. Res. Comm. 165: 1177-1183), enzymes such as juvenile hormone esterase (Bonning, B. C. et al. [1997] Proc. Natl. Acad. Sci. USA 94:6007-6012), and insect-specific toxins derived from venomous species such as scorpions and parasitic wasps (McCutchen, B. F. and Hammock, B. D. [1994] in Natural and Derived Pest Management Agents, Hedin, P. et al. [eds.], #551 ed., Washington, D.C.: Am. Chem. Soc., pp. 348-367. ACS Symposium Series; Hughes, P. R. et al. [1997] J. Invert. Pathol. 69:112-118; Lu, A. et al. [1996] in Biological control: theory and applications in 1996. 7:320; Gershburg, E. et al. [1998] FEBS Lett. 422:132-136; Jarvis, D. L. et al. [1996] in Biological control: theory and applications in 1996,7:228). These insecticidal proteins and peptides cannot be exploited for aphid control at present, because no system exists to deliver them into the hemocoel. Baculoviruses do not infect aphids, and although viruses such as Rhopalosiphum padi virus are known that infect aphids, there is insufficient knowledge of their biology and genetic structure for engineering for aphid control. Furthermore, the release of replicating, transgenic viruses poses greater risk to the ecosystem than expression of nonreplicating viral genes limited to the crop plant, as we disclose here. In the present invention, transgenically expressed, nonreplicating, plant viral structural proteins deliver insecticidal proteins or peptides into the hemolymph of aphids.

The toxin AaIT, that is derived from the venom of the North African scorpion Androctonus australis Hector, has a unique specificity for the nervous system of insects and some other arthropods such as crustaceans (Zlotkin, E. [1986] in Neuropharmacology and pesticide action, Chicester: Horwood; DeDianous S, et al. [1987] Toxicon 25:411-417). AaIT has no mammalian toxicity. Its strict selectivity for insects has been documented by toxicity assays, electrophysiological studies and binding assays (Zlotkin [1986] supra). AaIT is toxic to all insect species tested. These include over 15 species representing five orders of holo and hemimetabolous insects (Diptera, Coleoptera, Dictyoptera, Orthoptera and Lepidoptera) (Gershburg, E. et al. [1998] supra; Zlotkin [1986] supra; Herrmann, R. et al. [1990] Insect Biochemistry 20:625). The rapid excitatory paralysis induced by AaIT results from repetitive firing of the insect's motor nerves with resulting massive and uncoordinated stimulation of the respective skeletal muscles (Walther, C. et al. [1976] J. Insect Physiol. 22:1187-1194). The insecticidal activity of injected AaIT shows that this toxin is among the most potent toxic compounds to insects. AaIT has a molecular weight of only 8 kDa and has four disulfide bridges giving a highly organized conformation (Darbon, H. et al. [1982] Int. J. Peptide Protein Res. 20:320-332).

AaIT does not penetrate the lipophilic cuticle of insects (DeDianous, S. et al. [1988] Pestic. Sci. 23:35-40). To exploit this toxin for insect pest control purposes, various baculoviruses have been engineered to express AaIT (Gershburg, E. et al. [1998] supra; Jarvis, D. L. [1996] supra; Maeda, S. et al. [1991] Virology 184:777-780; McCutchen, B. F. et al. [1991] Bio/Technol. 91:848-852; Stewart, L. M. D. et al. [1991] Nature 352:85-88). These viruses infect the tissues of lepidopteran larvae and recombinant AaIT produced by the virus is exported from the virus-infected cell into the body cavity, resulting in paralysis of the insect. Expression of AaIT is highly effective for control of lepidopteran pest species and significantly reduces the amount of feeding damage caused. Because the nerves (the target site of AaIT) of Lepidoptera are unique in being covered by glial cells which act as a barrier to the toxin, AaIT is even more toxic to nonlepidopteran species. However, because baculoviruses do not infect aphids, they cannot be used for aphid control without modification. Also, because the site of action of the toxin is the nerves, transgenic plants expressing AaIT alone would not be aphid resistant because ingested toxin would pass through the insect.

SUMMARY OF THE INVENTION

The invention involves combining a peptide toxin effective against insects, including but not limited to thrips, leaf hoppers, and beetles, with a transport peptide capable of facilitating transfer of the peptide toxin from the gut of an insect to the hemocoel. The combination can be effected by a fusion of genetic material encoding the peptide toxin and the transport peptide, such that expression of the genetic material fusion results in synthesis of a fusion protein combining the functions of both the toxin and the transport protein. Ingestion of the fusion protein by the sucking insect transfers the fusion protein into the insect's gut from which it is transferred into the hemocoel due to the functional activity of the transport peptide where the toxin exerts its toxic effect upon the insect. In a preferred embodiment, the invention is effective in control of such sucking insects as aphids, whiteflies and the like, and other vectors that transmit viruses in a circulative manner. A variety of transport peptides can be employed, including a coat protein, or transport function domain thereof, of a plant virus for which the sucking insect is a vector in the transmission of the virus from plant to plant. For example, the coat proteins and readthrough domains of certain aphid-transmitted luteoviruses provide transport function in the case of aphids, while the coat-proteins of whitefly-transmitted gemini viruses provide transport function in the case of whiteflies.

Any peptide having a toxic effect when present in the circulatory system of a target insect can, in principle, be incorporated into a toxic fusion protein. Virus proteins that cross the gut barrier of an insect or other pest organism can be exploited for direct delivery of a variety of toxic agents which are active only in the body cavity of that organism. The requirements for these toxic agents include that (1) the agent should be specific for the targeted pest without mammalian toxicity; (2) the agent should be active at low levels; (3) the agent should have a rapid effect on the host. These toxic agents include both toxins that act on the nervous system of insects, and physiological effectors which disrupt regulation of homeostasis in the insect, resulting in feeding inhibition and/or death. A variety of such toxins and physiological effectors have already been exploited specifically for the control of lepidopteran (moth) pests by recombinant baculovirus expression (see Tables 1 and 2 for current lists). The insect-specific neurotoxins have generally been considered to be more effective than physiological effectors, in part because of feed-back regulatory systems in the insect for the latter. There is an ongoing effort within commercial, government and academic laboratories to isolate toxins that specifically target the insect nervous system from a variety of organisms that use venoms to immobilize their prey. The virus coat protein delivery system can be exploited for delivery of all of these agents in an array of pest species.

TABLE 1

Recombinant baculoviruses expressing neurotoxic peptides.

| | | | Efficacy of virus | | | |
|---|---|---|---|---|---|---|
| Origin of toxin | Toxin | Virus Name | Reduction in $ET_{50}$ | Reduction in feeding | Lepidopteran host tested | Reference |
| MITE | | | | | | (Tomalski and Miller, 1991; |
| Pyemotes tritici straw itch mite | TxP-1[a] | vSp-Tox34 | 40% | | Trichoplusia ni | Tomalski and Miller, 1992) (Lu et al., 1996) |
| | | vp6.9tox34 | 60% | T. ni, | | |
| | | HzEGTDA−26tox34 | 40% | | Spodoptera frugiperda Helicopverpa zea | (Popham et al., 1997) |
| SCORPION | | | | | | |
| Androctonus australis North African (Algerian) scorpion | AaIT | AcST-3 AcAaIT BmAaIT | 10-38% | 55-62% | T. ni Heliothis virescens Bombyx mori[c] | (Cory et al., 1994; Hoover et al., 1995; Maeda et al., 1991; McCutchen et al., 1991; Stewart et al., 1991) |
| | | Ro6.9AaIT | 35% | | Ostninia nubilalis | Bonning & Harrison[d] |
| Leiurus quinquestriatus hebraeus Israeli yellow scorpion | LqhIT1 LqhIT2 LqhIT3 LqhαIT[b] | AcLIT1.p10 AcLIT2.pol BmLqhIT2 AcLqhIT3 AcLα22 | 24% 32% 20% 35% | | Helicoverpa armigera H. armigera B. mori[c] H. virescens H. armigera | (Gershburg et al., 1998) (Gershburg et at., 1998) Imai, Aly & Maeda[d] (Herrmann et al., 1995) (Chejanovsky et al., 1995) |
| SEA ANEMONE | | | | | | |
| Anemonia sulcata | AsII | vSAt2p+ | 38% | 48% | T. ni | (Prikhod'ko et al., 1998; Prikhod'ko et al., 1996) |

TABLE 1-continued

Recombinant baculoviruses expressing neurotoxic peptides.

| Origin of toxin | Toxin | Virus Name | Efficacy of virus | | Lepidopteran host tested | Reference |
| | | | Reduction in $ET_{50}$ | Reduction in feeding | | |
|---|---|---|---|---|---|---|
| *Stichadactyla helianthus* SPIDER | ShI | vSShlp+ | 36% | | *T. ni* | (Prikhod'ko et al., 1996) |
| *Agelenopsis sulcata* American funnel web spider | μ-Aga-IV | vMAg4p+ | 37% | 50% | *Spodoptera frugiperda* *T. ni* | (Prikhod'ko et al., 1998; Prikhod'ko et al., 1996) |
| *Tegenaria agrestis* | TalTX-1 | vTalTX-1 | 18-33 | 16-39% | *T. ni* *Spodoptera exigua* *H. virescens* | (Hughes et al., 1997) |
| *Diguetia canities* primitive weaving spider | DTX9.2 | vAcDTX9.2 | 9-24 | 30-40% | *T. ni* *S. exigua* *H. virescens* | (Hughes et al., 1997) |
| TOXIN COMBINATION | μ-Aga-VI+ AsII | vMAg4Sat2 | 43% | 63% | *T. ni* *S. frugiperda* | (Prikhod'ko et al., 1998) |

[a] Mechanism of action currently unknown
[b] Non selective neurotoxin. Weak mammalian toxicity.
[c] Larvae infected by injection
[d] unpublished data

TABLE 2

Optimization of baculovirus insecticides by expression of physiological effectors.

| Agent | Virus | Target | Physiological effect | Efficacy/ Reduction in $ST_{50}$ | Lepidopteran host tested | Reference |
|---|---|---|---|---|---|---|
| diuretic hormone | BmDH5 | Malpighian tubules | disrupt water balance | 20% | *B. mori*[a] | (Maeda, 1989) |
| pheromone biosynthesis activating neuropeptide (PBAN) | AcBX-PBAN | pheromone biosynthesis | unknown (5 peptides expressed) | 19-16% | *T. ni* | (Ma et al., 1998) |
| juvenile hormone esterase (modified) | AcJHE-SG | unknown | disruption of molt or contraction paralysis | 30% 66% reduction in feeding damage | *T. ni* *H. virescens* | (Bonning et al., 1995) |
| | AcJHE-KK | juvenile hormone | disruption of lysosome targeting in pericardial cells | 50% reduction in feeding damage | *H. virescens* | (Bonning et al., 1997) |
| chitinase | vAcMNPV.chi | chitin | | 22-23% | *S. frugiperda*[a] | (Gopalakrishnan et al., 1995) |
| maize URF13 | BV13T BV13.3940 | mitochondria | proteins bind to cell membranes | 40% | *T. ni*[a] | (Korth and Levings, 1993) |
| antisense c-myc | MycAS | cell regulation | | 15-20% feeding inhibition | *S. frugiperda*[a] | (Lee et al., 1997) |
| egt deletion | vEGTDEL | unclear - deletion of virus egt gene removes virus inactivation of ecdysteroids | degeneration of Malpighian tubules | 20% | *S. frugiperda* | (Flipsen et al., 1995a; Flipsen et al., 1995b; O'Reilly and Miller, 1991) |

[a] Larvae injected with virus

All toxins listed in Table 1, (except for TxP-1 and TalTX-1 whose mechanisms of action are currently unknown), disrupt regulation of the sodium channels in the insect nervous system. These neurotoxins act at several different sites on the sodium channel, some being excitatory in action resulting in contractile paralysis, and others inhibitory resulting in slow, flaccid paralysis. Co-injection of insect-selective neurotoxins showed that toxins that act at different sites on the sodium channel can act synergistically (Hermann, R. et al. [1995] *Toxicon* 33:1099-1102), and hence delivery of multiple toxins to the targeted pest can further improve the pesticidal efficacy of the invention. Furthermore, application of low levels of pyrethroid insecticide (which targets the sodium channels) or a carbamate insecticide (which targets acetylcholinesterase in the nervous system), act synergistically with at least one of the insect specific neurotoxins (McCuthen B. F., [1997] *J. Ec. Entomol.* 901171-1180). Accordingly, certain chemical insecticides applied at very low doses ($LC_{10}$-$LC_{20}$) can also enhance the efficacy of the virus coat protein delivery system when such neurotoxins are used.

The invention allows the person or ordinary skill in the art to construct a fusion protein combining a transport peptide and an insect-toxic peptide for control of a large range of insects that damage a large variety of plants of commercial importance. Such plants include, but are not limited to, wheat, barley, oats, rice, corn (especially maize streak virus in Africa and sweet corn in the US) potato, sugar beet, soybean, tomato, citrus (orange, lemon, lime, grapefruit), Rosaceae (rose), fruit trees (plum, apple, cherry, peach, pear), lettuce, french bean, sugar cane, papaya, squash, cucurbits, banana, cassava, sweet potato, grape, all ornamentals and the like, including other members of the plant families to which the foregoing plants belong.

The family Aleyrodidae (whiteflies), family order *Homoptera*, including the Aphidae (aphids), family phylloxeridae (the phylloxera pests of grape), the superfamily Fulgoroidae (plant hoppers, the family cicadellidae (leaf hoppers), the Order Thysanoptera (thrips), and the Order Coleoptera, especially the family Chrysomilidae (leaf beetles) and the Genus *Diabrotica* (corn rootworm). With regard to the beetles, e.g. corn rootworm, it is known that the adults can transmit circulative viruses, the transport peptides of which can be used for control of those insects.

The fusion protein can be delivered to the target insect by any of a variety of ways. However, a preferred method is to deliver the fusion protein during the natural feeding activity of the insect, from the plant itself. The invention therefore includes plant-expressible gene constructs which can be used to transform a plant such that the plant expresses the fusion protein in its sap or tissues where insect feeding occurs. Transgenic plants, capable of expressing a transport peptide-toxin peptide fusion protein are thereby rendered resistant to the damage caused by insects and the diseases transmitted by them. The plant expressible gene constructs can be expressed either constitutively, or in an inducible manner, such as during a desired developmental stage, in a desired tissue, at a desired time or under desired environmental conditions. Constructs can be expressed from stably integrated transgenes or via transient vectors. Modified plant viruses can also be used as a spray on the surface of the crop plant, where ingestion by the target insect introduces the toxic protein to the insect gut.

The invention herein is described by reference to the combination of a luteovirus coat protein and a scorpion toxin, for aphid control. However, it will be understood that other embodiments and variations, according to the principles taught herein and combined with those known in the art, can be made as part of the present invention. The invention therefore includes delivery of any protein to the hemocoel of any arthropod or other organism (nemotode) that takes up and transmits viruses in a circulative or non-circulative fashion.

BRIEF DESCRIPTION OF THE FIGURES

FIGS. 4A and 4E show the constructs, AaIT6 and AaIT11, respectively.

FIG. 6 illustrates Northern blot hybridization showing accumulation of wildtype and AaIT-expressing viral RNAs in oat protoplasts.

DETAILED DESCRIPTION OF THE INVENTION

Figure 1:
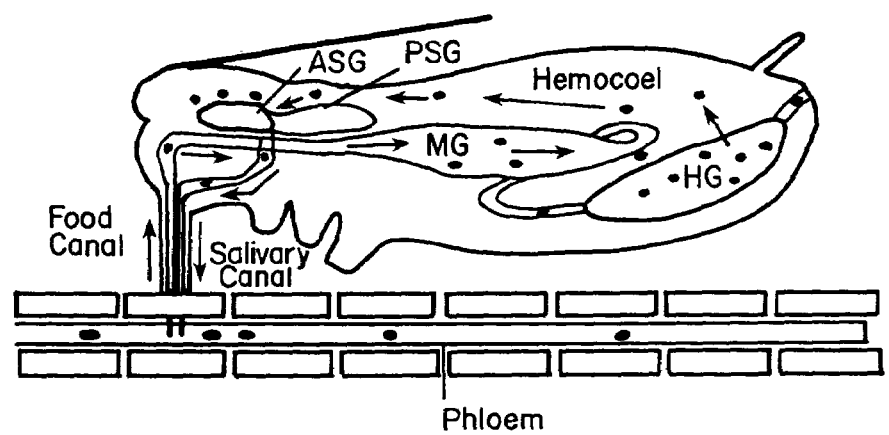
FIG. 1 is a diagrammatic view of an aphid in saggital section feeding upon a plant, showing in general the route of transmission of a luteovirus.
Figure 2:
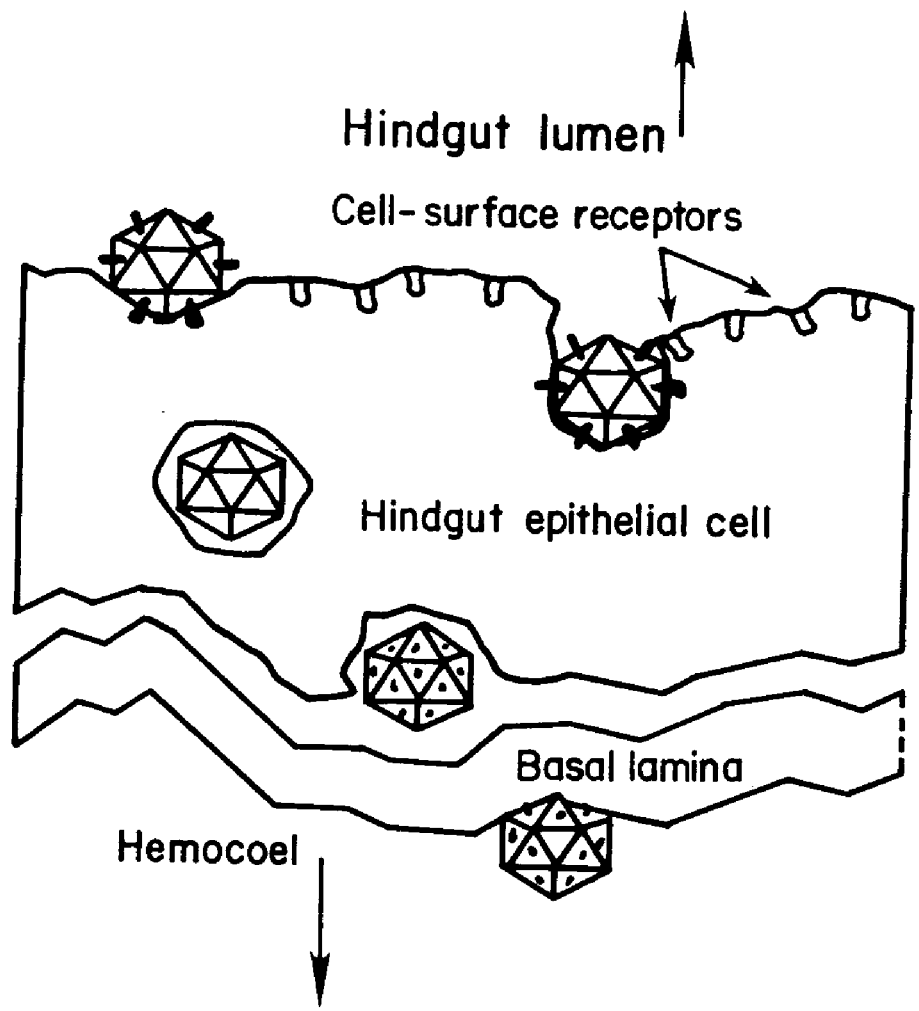
FIG. 2 is a diagrammatic view of the process of receptor-mediated endocytosis of a luteovirus from the hindgut to the aphid hemocoel.

The term "peptide" is used to refer to any poly-amino acid, without limitation as to size or molecular weight. As used herein, "peptide" includes such terms of common usage in the art as "oligo-peptide," "polypeptide" and "protein."

The term "transport peptide" is herein defined as that peptide segment which is necessary for transport of a circulatively-transmitted virus from the gut to the hemocoel of an insect. A transport peptide can include all, or a portion of, a virus coat protein or other virus protein and can also include all or part of a readthrough domain. That portion of a coat protein or other virus protein which constitutes a transport peptide is termed a component of the coat or other protein. It will be understood in the art that a specific interaction exists between the transport peptide of a virus and the insect host of the virus. A peptide intended to serve as a transport peptide for a given insect species is obtained from a circulatively transmitted virus that is known to infect that insect, as would be understood in the art.

The term "insect-toxic peptide" refers to any peptide which is toxic to an insect when delivered to the appropriate site of action of the insect. The present invention is directed to toxic peptides which exert their effect when delivered to the hemocoel of the insect. Examples of known insect-toxic peptides are given in Table I; however, the number of such peptides that become known is increasing, and any such peptide can be employed in the present invention.

"Readthrough domain" (RTD) is the term used to denote a DNA coding segment, or open reading frame which is situated downstream of a stop codon, in the direction of translation, and whose presence results in synthesis of a fusion protein composed of amino acids encoded upstream of the stop codon and amino acids encoded downstream of the stop codon. The presence of a RTD is indicated by an increased frequency of synthesis of a protein having amino acids encoded by the ORF downstream of the stop codon (readthrough) compared to the frequency of synthesis where the RTD is not present. In the case of an RTD situated downstream of a coat protein gene, the presence of the RTD results in a portion of viral coat proteins having a C-terminal peptide extension. In the case of BYDV, the RTD provides a convenient means for constructing a fusion protein that includes an insect-toxic peptide. The peptide encoded by the RTD of BYDV is not necessary for function as a transport protein, although it may play a role in transport function.

A segment of coding DNA is "expressed" in vivo or in vitro, if the DNA is transcribed or if the transcription product is translated. Expression can result in synthesis of an mRNA or of a protein encoded by the coding DNA.

"Associated with/operatively linked" refer to nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric gene" is a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature. A chimeric gene having operatively linked coding and expression control segments is also referred to herein as an "expression cassette."

To "control" insects means to inhibit, through a toxic effect, the ability of insect pests to survive, grow, feed, and/or reproduce, or to limit insect-related damage or loss in crop plants. to "control" insects may or may not mean killing the insects, although it preferably means killing the insects.

To "deliver" a toxin means that the toxin comes in contact with an insect, resulting in toxic effect and control of the insect. The toxin can be delivered in many recognized ways, e.g., orally by ingestion by the insect or by contact with the insect via transgenic plant expression, formulated protein compositions(s), sprayable protein composition(s), a bait matrix, or any other art-recognized toxin delivery system.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant tissue" as used herein means a group of plant cells organized into a structural and functional unit. Any tissue of a plant in plants or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase II and initiates transcription of the DNA. The promoter region may also include other elements that act as regulators of gene expression.

A "protoplast" is an isolated plant cell without a cell wall or with only part of the cell wall.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g. a bacterium or plant, which does not contain the heterologous nucleic acid molecule.

Because luteovirus CP and CP-RTD's are taken up efficiently into the hemocoel, they make ideal vehicles for transporting proteins that are translationally fused to them. FIG. 1 is useful to visualize the circulative pathway of luteovirus transmission (from Chay et al., [1996*] Virol.* 219:57-65). HG=hindgut; MG=midgut; ASG=accessory salivary gland; PSG—primary salivary gland.

FIG. 2 is a diagram of the proposed mechanism of receptor-mediated endocytosis of luteoviruses from the hindgut into the aphid hemocoel (from Gray, [1996*] Trends Microbiol.* 4:259-264). The virus binds to specific receptors on the epithelial cells of the hindgut and is taken up by endocytosis. The virus-containing vesicle then fuses with the basal plasmalemma of the epithelial cell, and the virus is released into the hemolymph of the aphid. We exploit these properties to deliver nonviral proteins known to be toxic only when present in the aphid hemocoel. An example of such a toxin is AaIT. This gene fusion results in an effective aphicidal transgene product because the protein is toxic at low levels in the hemolymph (Gershburg, E. et al. [1998] supra; Jarvis, D. L. [1996] supra). Equally important, this approach is unlikely to harm nontarget organisms because the toxin is active only in the insect, and the CP-RTD of luteoviruses is specific for aphids. The toxin is also harmless to mammals. Not only will this strategy provide resistance to damage caused directly by the aphid, but it will effectively provide resistance to numerous aphid-transmitted viruses. For example, a variety of diseases caused both by luteo- and nonluteoviruses would be controlled by death of the aphid vector, *Myzus persicae*. By using a resistance gene that targets aphid species, the invention will have a significant impact both on control of aphids and on control of aphid-transmitted diseases.

Aphids are among the most economically important pest insects of temperate agriculture. They cause yield losses by direct feeding, by the honeydew produced which encourages the growth of harmful sooty molds and, most importantly, by transmission of plant viruses (Harris, K. F. and Maramorosch, K., eds., [1977*] Aphids as Virus Vectors*, Academic Press, New York; Sylvester, E. S. [1989] in *Aphids. Their biology natural enemies and control*, Minks et al. [eds.]), Amsterdam: Elsevier, vol C., pp 65-88). In Britain losses due to aphids themselves average $150 million/year (Tatchell, G. M. [1989*], Crop Protection* 8:25-29). In the U.S., losses due to the recently introduced Russian wheat aphid *Diuraphis noxia*, alone were $200 million by 1989 (Burton, R. L. [1989], "The wheat aphid," 2nd Annual Report of the Agricultural Research Station, USDA, p. 28). Aphid-transmitted viruses cause losses of a similar order. In the U.S., typical 5% yield losses in cereals caused by BYDVs would be valued at nearly $500 million (1989 prices) (Hewings, A. D. et al. [1995], in *Barley Yellow Dwarf:* 40 *Years of Progress*, D'Arcy, C. J. et al., eds., APS Press, pp. 75-106). Other aphid transmitted viruses cause even greater losses in a wide variety of crops and trees (Miles, P. W. [1989] in *Aphids. Their biology natural enemies and control*, Minks, A. K. et al., eds., Amsterdam: Elsevier, vol C, pp. 23-47). These examples show the immense scale of aphid problems.

Although chemical, genetic, and biological control strategies have met with success, all have their limitations and drawbacks. Many tons of fossil fuel are consumed in the manufacture and application of insecticides that are used specifically to control aphids and the viral diseases they transmit. The widespread use of chemical sprays can harm wildlife. Thus, alternative, environmentally acceptable means of aphid control are needed to maintain both farm incomes and sustainable food production.

Biological control methods are limited to specific aphid-parasite interactions and are most effective on perennial crops. The use of genetic aphid resistance reduces the necessity for chemical control, but natural resistance genes are limited. A transgenic approach to aphid resistance allows rapid introduction of new kinds of genes into popular cultivars without the generations of back-crossing needed for introducing genes by conventional breeding. The same constructs can be used for engineering all crops susceptible to aphid attack, because luteoviruses are taken up into the hemocoel of both vector and nonvector aphid species. The invention provides a new weapon in the battery of strategies that are necessary to avoid loss of control through development of aphid resistance to current control measures.

The DNA sequence and translated amino acid sequence of barley yellow dwarf virus coat protein and readthrough domain are given in Table 3 and in SEQ ID NO:1 (nucleotide sequence) and SEQ ID NO:2 (amino acid sequence). The coat protein has the sequence of the first 198 amino acids encoded. Immediately following the codon for amino acid 200 is a TAG (amber) stop codon followed, immediately by GTA, in the same reading frame, encoding a valine. The coat protein-readthrough fusion extends from amino acids 1-669. In Table 3, nucleotide numbers and corresponding encoded amino acid numbers are presented in pairs separated by a slash mark. For example, in the first line of Table 3, the numbers 31/11 designate nucleotide #31, a C directly under numeral 3, and amino acid #11, encoded by the codon beginning at nucleotide #31 (CGC).

The steps of making and evaluating an embodiment of the invention include the following:
1. Construct and express CP-RTD-AaIT fusions:
   A. In a replicating BYDV-PAV as a transient expression system.
   B. In the baculovirus expression system for purification of recombinant proteins.
2. Measure aphid toxicity of CP-RTD-AaIT fusion proteins. Determine:
   A. Aphicidal efficacy of ingested CP-RTD-AaIT fusion proteins.
   B. Insecticidal efficacy of injected CP-RTD-AaIT fusion proteins.
   C. Presence of AaIT in the aphid hemocoel.

TABLE 3

DNA sequence 1956 b.p. ATGAATTCAGTA . . . CAATTCCAGTGA linear

```
1   /   1                                         31  /   11
ATG AAT TCA GTA GGT CGT AGA GGA CCT AGA           CGC GCA AAT CAA AAT GGC ACA AGA AGG AGG
met asn ser val gly arg arg gly pro arg           arg ala asn gln asn gly thr arg arg arg 61  /   21                                        91  /   31
CGC CGT AGA ACA GTT CGG CCA GTG GTT GTG           GTC CAA CCC AAT CGA GCA GGA CCC AGA CGA
arg arg arg thr val arg pro val val val           val gln pro asn arg ala gly pro arg arg 121 /   41                                        151 /   51
CGA AAT GGT CGA CGC AAG GGA AGA GGA GGG           GCA AAT TTT GTA TTT AGA CCA ACA GGC GGG
arg asn gly arg arg lys gly arg gly gly           ala asn phe val phe arg pro thr gly gly 181 /   61                                        211 /   71
ACT GAG GTA TTC GTA TTC TCA GTT GAC AAC           CTT AAA GCC AAC TCC TCC GGG GCA ATC AAA
thr glu val phe val phe ser val asp asn           leu lys ala asn ser ser gly ala ile lys 241 /   81                                        271 /   91
TTC GGC CCC AGT CTA TCG CAA TGC CCA GCG           CTT TCA GAC GGA ATA CTC AAG TCC TAC CAT
phe gly pro ser leu ser gln cys pro ala           leu ser asp gly ile leu lys ser tyr his 301 /  101                                        331 /  111
CGT TAC AAG ATC ACA AGT ATC CGA GTT GAG           TTT AAG TCA CAC GCG TCC GCC AAT ACG GCA
arg tyr lys ile thr ser ile arg val glu           phe lys ser his ala ser ala asn thr ala 361 /  121                                        391 /  131
GGC GCT ATC TTT ATT GAG CTC GAC ACC GCG           TGC AAG CAA TCA GCC CTG GGT AGC TAC ATT
gly ala ile phe ile glu leu asp thr ala           cys lys gln ser ala leu gly ser tyr ile 421 /  141                                        451 /  151
AAT TCC TTC ACC ATC AGC AAG ACC GCC TCC           AAG ACC TTC CGG TCA GAG GCA ATT AAT GGG
asn ser phe thr ile ser lys thr ala ser           lys thr phe arg ser glu ala ile asn gly 481 /  161                                        511 /  171
AAG GAA TTC CAG GAA TCA ACG ATA GAC CAA           TTT TGG ATG CTC TAC AAG GCC AAT GGA ACT
lys glu phe gln glu ser thr ile asp gln           phe trp met leu tyr lys ala asn gly thr 541 /  181                                        571 /  191
ACC ACT GAC ACG GCA GGA CAA TTT ATC ATT           ACG ATG AGT GTC AGT TTG ATG ACG GCC AAA
thr thr asp thr ala gly gln phe ile ile           thr met ser val ser leu met thr ala lys 601 /  201                                        631 /  211
TAG GTA GAC TCC TCA ACA CCG GAA CCA AAA           CCT GCA CCG GAA CCA ACA CCA ACC CCC CAG
AMB val asp ser ser thr pro glu pro lys           pro ala pro glu pro thr pro thr pro gln 661 /  221                                        691 /  231
CCA ACG CCG GCT CCA CAG CCC ACA CCT GAA           CCA ACT CCT GCA CCT GTC CCC AAA AGA TTC
pro thr pro ala pro gln pro thr pro glu           pro thr pro ala pro val pro lys arg phe
```

TABLE 3-continued

DNA sequence 1956 b.p. ATGAATTCAGTA . . . CAATTCCAGTGA linear

```
721 /  241                              751 /  251
TTC GAG TAT ATC GGA ACT CCT ACC GGT ACA ATC TCG ACT AGA GAG AAC ACT GAC AGT ATA
phe glu tyr ile gly thr pro thr gly thr ile ser thr arg glu asn thr asp ser ile 781 /  281                              811 /  271
TCT GTC AGC AAG CTC GGT GGA CAG TCG ATG CAG TAC ATT GAG AAT GAG AAA TGT GAA ACG
ser val ser lys leu gly gly gln ser met gln tyr ile glu asn glu lys cys glu thr 841 /  281                              871 /  291
AAA GTC ATC GAT TCC TTT TGG AGC ACT AAC AAC AAC GTT TCT GCG CAA GCA GCT TTC GTT
lys val ile asp ser phe trp ser thr asn asn asn val ser ala gln ala ala phe val 901 /  301                              931 /  311
TAT CCA GTG CCA GAG GGA TCA TAC AGC GTT AAC ATT TCG TGC GAA GGC TTC CAG TCA GTT
tyr pro val pro glu gly ser tyr ser val asn ile ser cys glu gly phe gln ser val 961 /  321                              991 /  331
GAC CAC ATC GGT GGC AAC GAG GAC GGC TAT TGG ATT GGT TTA ATT GCC TAC TCC AAT TCG
asp his ile gly gly asn glu asp gly tyr trp ile gly leu ile ala tyr ser asn ser 1021 /  341                             1051 /  351
TCT GGC GAT AAT TGG GGA GTT GGC AAT TAC AAA GGG TGC AGT TTT AAG AAT TTC TTG GCA
ser gly asp asn trp gly val gly asn tyr lys gly cys ser phe lys asn phe leu ala 1081 /  361                             1111 /  371
ACC AAC ACT TGG AGA CCA GGC CAC AAA GAT CTC AAG TTG ACT GAT TGC CAG TTC ACA GAT
thr asn thr trp arg pro gly his lys asp leu lys leu thr asp cys gln phe thr asp 1141 /  381                             1171 /  391
GGA CAA ATA GTT GAA AGG GAC GCC GTG ATG TCT TTC CAC GTA GAA GCA ACA GGC AAG GAT
gly gln ile val glu arg asp ala val met ser phe his val glu ala thr gly lys asp 1201 /  401                             1231 /  411
GCC AGC TTC TAC CTC ATG GCT CCC AAA ACA ATG AAA ACT GAC AAA TAC AAC TAT GTT GTC
ala ser phe tyr leu met ala pro lys thr met lys thr asp lys tyr asn tyr val val 1261 /  421                             1291 /  431
TCA TAT GGA GGG TAC ACA AAC AAG CGA ATG GAA TTC GGT ACC ATA TCT GTG ACA TGT GAT
ser tyr gly gly tyr thr asn lys arg met glu phe gly thr ile ser val thr cys asp 1321 /  441                             1351 /  451
GAA TCC GAT GTT GAG GCA GAA CGA ATA ACA AGG CAC GCT GAA ACG CCC ATA CGT TCT AAA
glu ser asp val glu ala glu arg ile thr arg his ala glu thr pro ile arg ser lys 1381 /  461                             1411 /  471
CAT ATT CTT GTT TCT GAG CGG TAT GCG GAA CCA TTG CCC ACC ATA GTC AAC CAA GGC TTG
his ile leu val ser glu arg tyr ala glu pro leu pro thr ile val asn gln gly leu 1441 /  481                             1471 /  491
TGT GAT GTG AAA ACT CCC GAG CAA GAA CAA ACA CTG GTG GAT GAA GAT GAC AGA CAA ACT
cys asp val lys thr pro glu gln glu gln thr leu val asp glu asp asp arg gln thr 1501 /  501                             1531 /  511
GTT TCT ACT GAA TCT GAT ATA GCA CTC CTG GAG TAT GAG GCT GCA ACA GCT GAG ATT CCG
val ser thr glu ser asp ile ala leu leu glu tyr glu ala ala thr ala glu ile pro 1561 /  521                             1591 /  531
GAT GCT GAA GAG GAC GTT TTG CCC TCC AAG GAA CAG TTG TCT TCA AAA CCA ATG GAT ACG
asp ala glu glu asp val leu pro ser lys glu gln leu ser ser lys pro met asp thr 1521 /  541                             1651 /  551
TCT GGC AAT ATA ATA CCA AAA CCC AAG GAA CCT GAA GTA CTT GGG ACA TAC CAA GGA CAG
ser gly asn ile ile pro lys pro lys glu pro glu val leu gly thr tyr gln gly gln 1681 /  561                             1711 /  571
AAC ATT TAT CCT GAA GAC GTA GCT CCA ATG GCG CGG CAG AAA TTG AGA GAA GCC GCG AAT
asn ile tyr pro glu asp val pro pro met ala arg gln lys leu arg glu ala ala asn 1741 /  581                             1771 /  591
GCG CCT TCC ACG CTA CTC TAT GAA AGA AGA ACC CCA AAG AAG AGT GGC AAC TTT TTA TCC
ala pro ser thr leu leu tyr glu arg arg thr pro lys lys ser gly asn phe leu ser 1801 /  601                             1861 /  611
AGA CTT GTA GAA GCG AAT AGG TCC CCT ACT ACT CCC ACT GCC CCA TCC GTG TCA ACT ACT
arg leu val glu ala asn arg ser pro thr thr pro thr ala pro ser val ser thr thr
```

TABLE 3-continued

DNA sequence 1956 b.p. ATGAATTCAGTA . . . CAATTCCAGTGA linear

```
1861 /  621                                1891 /  631
TCA AAC ATG ACA AGG GAG CAG CTC CGG GAG TAC ACT AGG ATT AGA AAT TCC AGC GGA ATC
ser asn met thr arg glu gln leu arg glu tyr thr arg ile arg asn ser ser gly ile 1921 /  641                                1951 /  661
ACA GCA GCA AAG GCG TAC AAG GCG CAA TTC CAG TGA
thr ala ala lys ala tyr lys ala gln phe gln OPA
```

Several factors must be considered regarding properties of the CP-RTD and the genes encoding them: (i) the regions of the genes that are required for expression of CP and RTD; (ii) domains in the CP-RTD proteins that facilitate stability in the gut, import into the hemocoel, and stability in the hemolymph; (iii) whether whole virus particles contribute to survival in the aphid digestive system and import into the hemolymph, or whether the fusion proteins themselves are sufficient; and (iv) the effect of different fusions of CP-RTD to AaIT on toxicity of AaIT. Various approaches are available for expression and testing of the constructs. One is to express the BYDV-AaIT fusions from replicating BYDV RNA in infected cells, followed by purification of the protein. The other is to express fusion proteins using the baculovirus expression system. The former approach has the advantage of serving as a rapid, high-level transient expression system in the plant cell which is the native environment in which the constructs are to be expressed as transgenes. The latter allows expression of the gene from DNA in the nucleus out of its viral context which is the case in transgenic plants, and it allows rapid purification of the protein product for direct assessment of its interaction with the aphid. Both approaches can be performed simultaneously.

1. Expression of CP-RTD-AaIT Fusion Proteins

A. BYDV-PAV Replication-expression System

Figure 3:
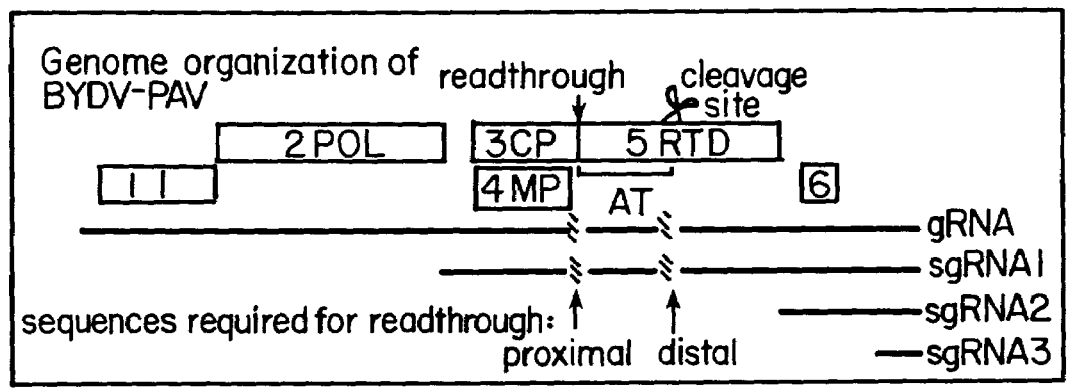
FIG. 3 is a diagram of the genome organization of BYDV-PAV.

The BYDV-PAV transient expression system allows one to identify CP-RTD-AaIT fusions with the greatest toxicity to the aphid. This reduces the number of constructs to be tested prior to stable plant transformation. FIG. 3 is a diagram of genome organization of BYDV-PAV. Bold lines indicate genomic (g) and subgenomic (sg) RNAs. ORFs are numbered as in Chay et al., (1996) *Virol.* 219:57-65. Coat protein (CP) and readthrough domain (RTD) are translated from sgRNA1. Portion of RTD required for aphid transmission (AT) is upstream of proteolytic cleavage site (scissors). Other functions: polymerase (POL) and systemic movement protein (MP).

Figure 4:
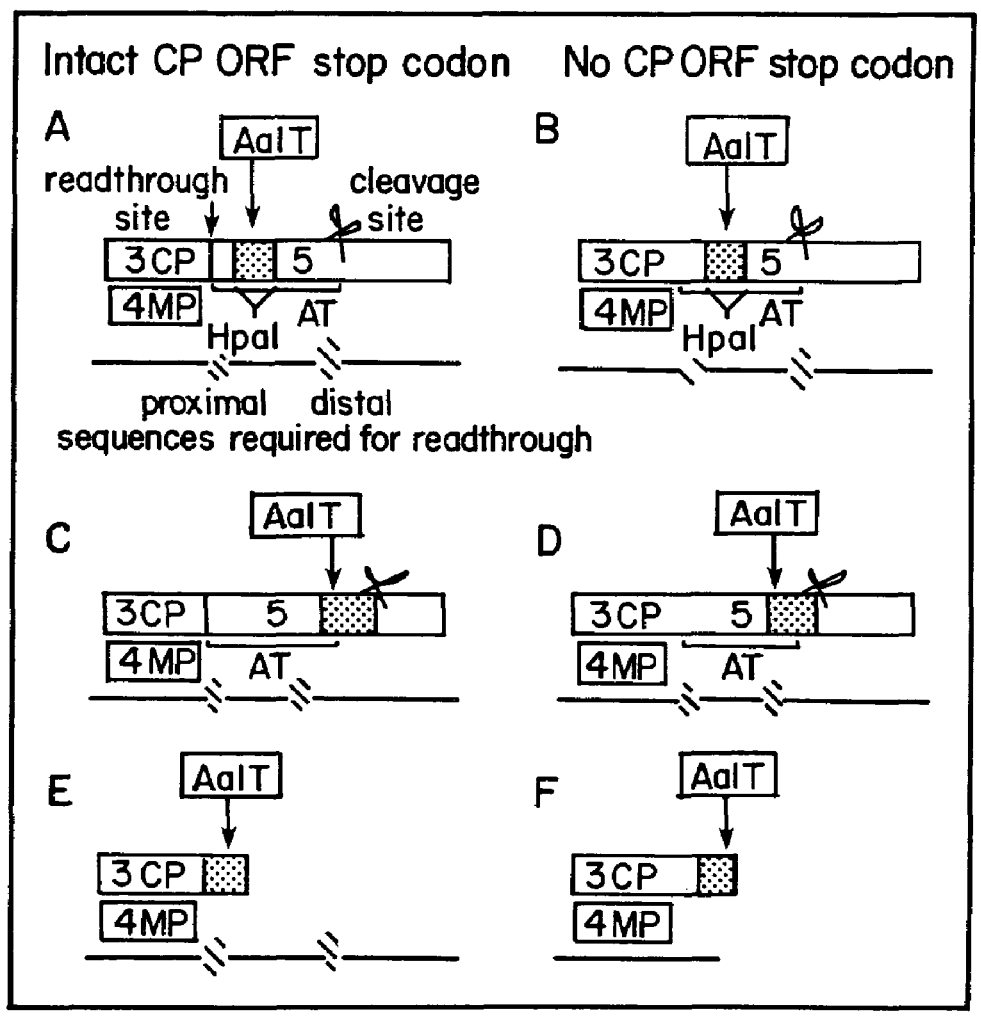
FIG. 4 is a diagram of different CP-RTD-AaIT fusions described herein.

In one embodiment, we removed the signal sequence that specifies secretion of AaIT (Maeda, S. et al. [1991] *Virology* 184:777-780; Adachi, T. et al. [1989] *J. Biol. Chem.* 264: 7681-7685), and placed the 200 nt region that codes for the mature AaIT protein into ORF 5 (that encodes the RTD) of pPAV6 (Di, R., et al. [1993] *Molec. Plant-Microbe Interactions* 6:444-453; Mohan, B. R., et al. [1995] *Virology* 212:186-195). In vitro transcription of pPAV6 with bacteriophage T7 polymerase yields full-length BYDV-PAV genomic RNA that is infectious in oat protoplasts (Mohan, B. R. et al. [1995] *Virology* 212:186-195). Hpa I sites were added to the 5' termini of primers flanking the AaIT gene termini in plasmid pTZ-AaHIT (McCutchen, B. F. [1991] supra). Following PCR and Hpa I digestion, the fragment was cloned into the unique H.a. I site in pPAV6, placing the AaIT coding region in-frame with ORF5, between the proximal and distal RT elements. FIG. 4 shows examples of CP-RTD-AaIT fusions to be tested. Scissors indicate approximate site of proteolytic cleavage of the RTD (Filichkin et al., [1994] *Virol.* 205:290-299; van den Heuvel et al., [1997] *J. Virol.* 71:7258-7265). Constructs were made with and without the AaIT stop codon and with and without the CP stop codon (FIGS. 4A,E). A construct corresponding to FIG. 4A, having the CP stop codon with an AaIT insert flanked by segments of the RTD was designated AaIT6, sequence given in SEQ ID NO:4. A second construct, having the CP stop codon but also containing the AaIT stop codon, corresponding to FIG. 4E was designated AaIT11, sequence given in SEQ ID NO:7. Translated amino acid sequences for AaIT6 and AaIT11 are shown in SEQ ID NO:5 and SEQ ID NO:6, respectively. These are tested for expression. The constructs are fully replicated and translated as has been shown with pPAV6. Transcripts containing the much larger 1.8 kb GUS gene inserted in ORF 5 replicated efficiently in oat protoplasts, and the readthrough required for expression of the RTD-GUS fusion was efficient (Brown, C. M. et al. [1996] supra).

Where the entire noncleaved portion of the RTD is required for stability of the fusion protein in hemolymph, we place the AaIT gene at the distal 3' end of this region. This is less likely to be disruptive to the aphid transmission function of RTD than an internal insertion. The proteolytic cleavage site in the RTD has been located at approximately amino acid 242 (Filichkin, S. A. [1994] supra; van den Heuvel, J. F. J. M. [1997] supra) which corresponds to base 4237 in ORF5 (FIGS. 3, 4). The cleavage site may is just downstream of the 3' end of the distal readthrough element (base 4219) (Brown C. M. et al. [1996] supra). It will be understood that inserting the AaIT downstream of the proteolytic cleavage site may result in loss of the AaIT from the virion before it reaches the hindgut. We insert the AaIT just upstream of the cleavage site so that after proteolytic cleavage, it is located very near the C-terminus of the RTD (FIGS. 4C,D). PCR mutagenesis methods (Landt, O. et al. [1990] *Gene* 96:125-128; Kuipers, O. P. et al. [1991] 19:4558) are used to introduce a convenient restriction site for this construct.

The relative efficacy of various constructs can be assessed, to optimize their activity under different conditions. For example, the activity of AaIT can be affected by fusion to viral proteins at its N and C termini as in the constructs in FIGS. 4A,C. The constructs that place the AaIT ORF at the end of the mature RTD (FIGS. 4C,D,E,F) increase the likelihood that AaIT will retain neurotoxicity, because AaIT will have only an N-terminal fusion. For all locations in which AaIT is inserted, we describe constructs with and without the AaIT stop codon. The presence of the AaIT stop codon, however, can result in less RTD being expressed, particularly in constructs with the AaIT ORF close to the CP stop codon (FIG. 4E). Thus, optimization of efficacy can involve a trade-off between viral and AaIT functions. In addition, increasingly large deletions of the RTD and the CP ORFs can be tested. The results allow one to map both the RNA domains required for readthrough of the CP ORF stop codon, and the protein domains required for stability in the aphid and transport of CP-RTD across the hindgut epithelium. The above-described mapping can more precisely define the sequences that contribute to efficient readthrough, and also define other regions suitable for insertion of an insect-toxic peptide coding sequence.

Protoplast Inoculation and Virus Purification

Infectious RNA transcripts and protoplasts were prepared as described previously (Koev, G. et al., [1999] J. Virol. 73:2876-2885; Mohan, B. R. et al., [1995] Virology 212: 186-195). Oa protoplasts were transfected with ~15 μg of viral RNA transcript by electroporation using the BTX Electro Square Porator T820 (San Diego, Calif.) with a single, 6 millisecond pulse at 300 V. For each construct, 6 individual samples were transfected. Protoplasts were harvested 48 hr after electroporation by centrifugation at 600×g for 6 min. The supernatant was removed and the pellets resuspended in 400 μl of 10 mM sodium phosphate buffer, pH 7.0. This suspension was sonicated for 2-3 sec. The sonicated protoplasts were centrifuged at 18,000×g (microcentrifuge) at 4° C. for 30 min. The supernatant was transferred to a new 1.5 ml tube and kept on ice at a cold room overnight or up to 48 hr. The supernatant was then microcentrifuged again at 18,000×g (4° C.) for 30 min. This centrifugation step was repeated as necessary until the supernatant was sufficiently clean. The supernatant was transferred to a 3 ml ultracentrifuge tube and the volume increased to 3 ml by addition of 10 mM sodium phosphate buffer, pH 7.0. The tube was then centrifuged at 90,000 rpm at 4° C. for 30 min (Beckman TL100 ultracentrifuge, rotor 66iB). The supernatant was discarded and the pellets resuspended in 80 μl of 10 mM sodium phosphate buffer, pH 7.0. This crude virus preparation was used for feeding aphids.

Membrane Feeding Assay

The aphid Rhopalosiphum padi was cultured on oat plants (cultivar Clintland64). Containers for aphid feeding were made from 6×15 mm petri dishes with black, opaque surfaces. An 18 mm hole was made in the center of the lower petri plate. Each petri dish may hold up to 150 aphids. The partially purified virus extracts (above) were diluted 1:1 or 1:2 in 50% sucrose and fed to virus-free aphids by placing 80-100 μl of the dilution between two Parafilm membranes which were stretched across the hole in the lower petri plate. The plates were placed>7 cm above a fluorescent light box covered with a yellow filter. After feeding at room temperature overnight (~16 hr), the numbers of surviving and dead aphids were counted. Natural mortality increased markedly with longer feeding periods.

An initial hurdle was to develop a satisfactory aphid feeding system in which aphids would feed rather than starving due to an aversion or inability to feed. Aphids fed efficiently and survival was high in the feeding apparatus described above. Other feeding systems, or placing aphids too close to the light source resulted in excessive mortality in the absence of virus or toxin. Secondly, the extract from uninfected protoplasts initially resulted in substantial aphid death, most likely resulting from aversion to feeding caused by a component in the crude cell extract. The problem was overcome by partially purifying the virus by the differential centrifugation steps described above.

Figure 5A:
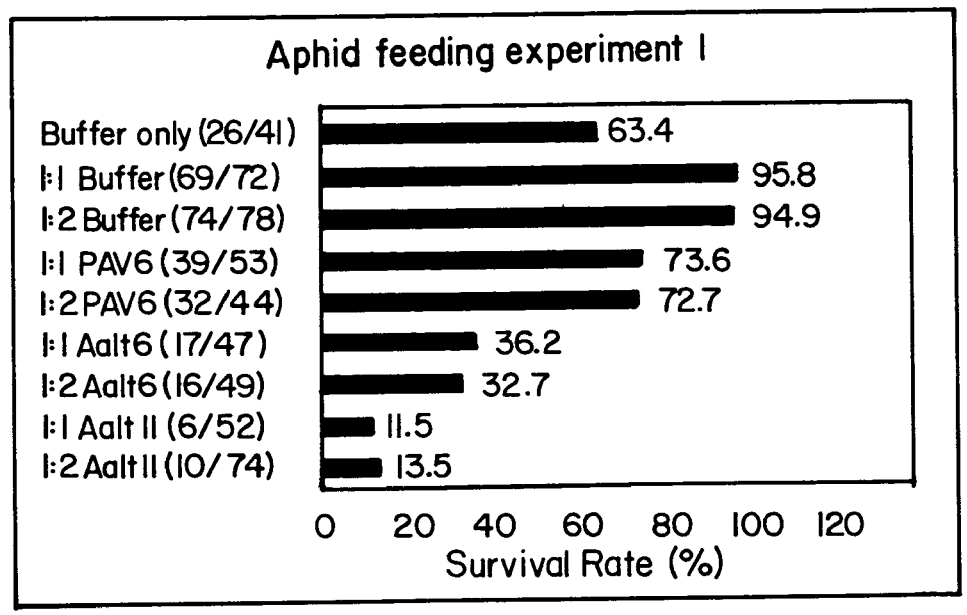
FIGS. 5A and 5B show the effect of wildtype and AaIT-expressing virus on aphid mortality. The nucleic acid sequences for the constructs, AaIT and AaIT11, are listed as SEQ ID Nos: 4 and 6, respectively.
Figure 5B:
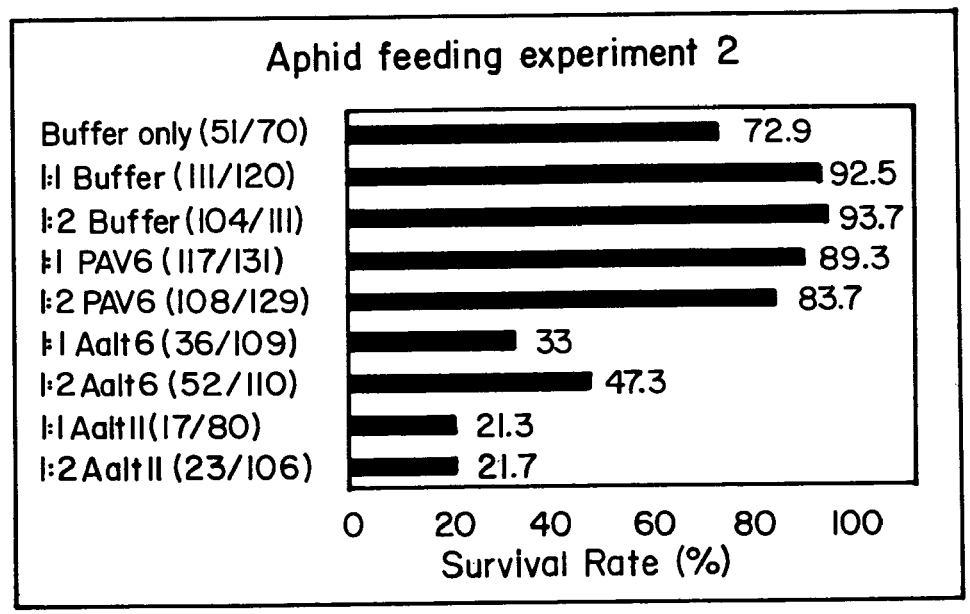

In two experiments, significantly more aphids died when feeding on extracts of virus harboring AaIT in the readthrough domain of the CP (FIGS. 5A and 5B), than died when feeding on negative control solutions. The negative control solutions included (i) sucrose solution, and (ii) extracts of protoplasts inoculated with wildtype virus. Visual inspection revealed that the cause of death of most of the aphids feeding on AaIT6 (FIG. 4A) or AaIT11 (FIG. 4E) virus did not resemble feeding aversion, because many aphids died on the membrane. Feeding aversion results in aphids walking around the petri plate, and dying farther from the membrane. Most importantly, the AaIT gene is clearly implicated in aphid death. Many more aphids died when feeding on virus encoding AaIT6 and AaIT11, than died when feeding on wildtype virus (from plasmid pPAV6) which differs from AaIT6 and AaIT11 constructs only by the absence of the AaIT gene (FIGS. 5A and 5B). There were no differences between the two dilutions of sucrose used in the feeding solutions tested for each transcript. The data in FIG. 5 were subjected to statistical analysis using 1-way ANOVA followed by Tukeys pairwise multiple comparison test for Buffer, PAV6, AaIT6 and AaIT11 (n=4 for each treatment): data for both 1:1 and 1:2 dilutions with 50% sucrose resulting in 25% (w/v) and 12.5% sucrose, respectively, final concentration. All comparisons are significantly different at $p<0.05$, i.e. survival ranks as follows: buffer treatment>PAV6>AaIT6>AaIT11.

Figure 6A:
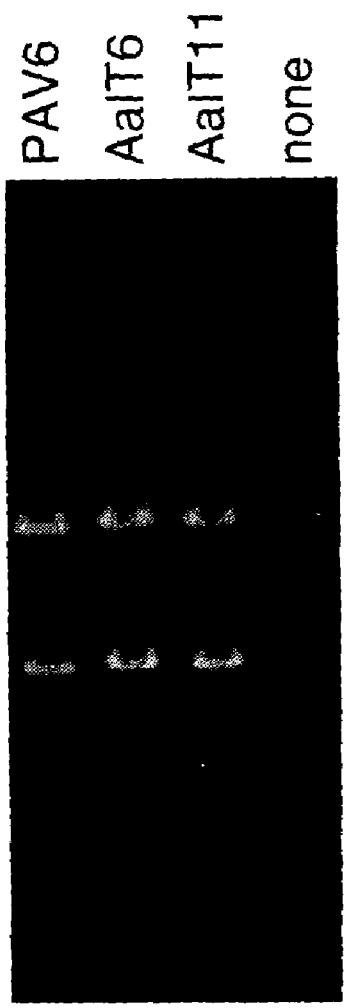
FIG. 6A shows ethidium bromide stained gel showing positions of ribosomal RNA.
Figure 6B:
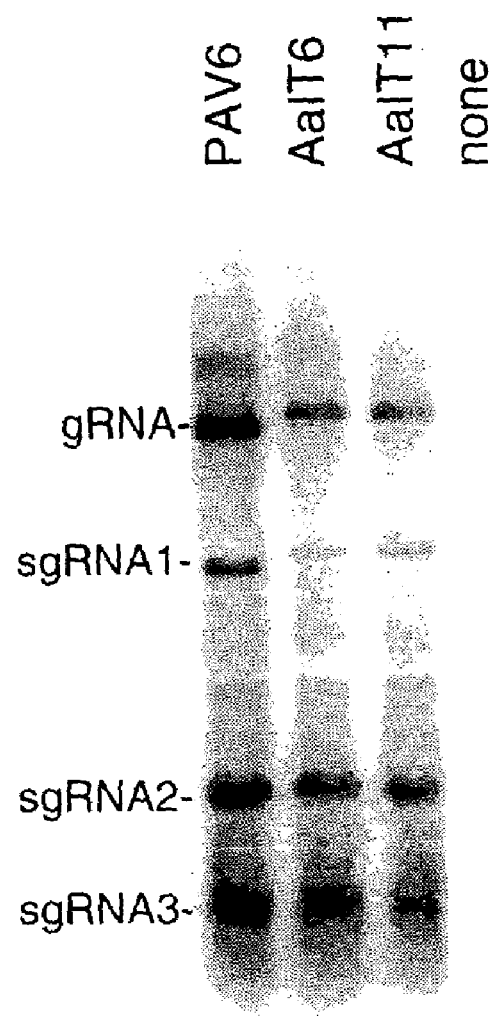
FIG. 6B shows positions of RNA probed with 32 P-labeled BYDV-specific antisense RNA. The nucleic acid sequences for the constructs, AaIT6 and AaIT11, are listed as SEQ ID NOS: 4 and 6, respectively.

AaIT mRNA has been observed in northern blot hybridizations. Total RNA was isolated 48 hr after inoculation of cells with the same constructs used for the feeding assays. 48 hr after inoculation, total RNA was extracted as in Koev, et al. (1999) supra, from aliquots of protoplasts inoculated with each of the constructs used in Experiment 2 above. RNA was separated by denaturing agarose gel electrophoresis and stained with ethidium bromide to verify loading of total RNA by visualization of ribosomal RNAs (FIG. 6A). The RNA was then blotted to nylon membrane, probed with $^{32}$P-labeled, BYDV-specific antisense RNA as described previously (Koev, et al. 1999). Radioactive bands were detected with a Phosphorimager (FIG. 6B). Mobilities of genomic RNA (gRNA) and the three subgenomic RNAs (sgRNA) produced during virus infection are indicated. sgRNA1 is the mRNA for the CP-RTD-AaIT fusion protein. Subgenomic RNAs 3 and 4 are small sgRNAs transcribed from the 3' end of the viral genome. As expected, sgRNA1 and gRNA from the AaIT6 and AaIT11-infected cells are slightly larger (migrate more slowly) than those from PAV6-infected cells, owing to the insertion of the 210 nt AaIT gene in the RTD, (FIG. 6B). Subgenomic RNA1 from AaIT6 and AaIT11 comigrates with highly abundant ribosomal RNA which partially obscures it in the northern blot hybridization. However, significant levels were still detected (FIG. 6A, lanes AaIT6 and AaIT11). The presence of AaIT mRNA (subgenomic RNA1) suggests that the AaIT fusion protein was being expressed. The fact that these levels were slightly lower than wildtype (FIG. 6B, lane PAV6) indicates that aphid mortality was not simply proportional to the amount of virus replication, but was correlated with the presence of the AaIT gene.

The higher mortality caused by AaIT1I compared to AaIT6 can be explained by the absence of a carboxyterminal fusion to the AaIT protein in AaIT11. AaIT6 has the RTD of the CP fused at both its amino- and carboxytermini (FIG. 4A and SEQ ID NO:4), whereas AaIT11 has its own stop codon (FIG. 4E and SEQ ID NO:6). Thus AaIT11 has only the aminoterminal fusion to RTD. Fusing additional amino acid sequences to proteins can cause mis-folding or folding such that the domain of interest is not exposed on the surface.

These results imply that most of the RTD (the portion downstream of AaIT) is not necessary for delivery of AaIT to the hemocoel. This is consistent with previous work showing that the RTD, while necessary for virus transmission by the aphid, is not necessary for delivery of the virus to the hemocoel (Chay, et al., [1996] supra; van den Heuvel, et al., [1997] supra).

These experiments allow one to evaluate the effects of a high ratio of CP:RTD compared to removal of the CP stop codon allowing 100% readthrough for translation of the CP-RTD-AaIT fusion. It is also possible that the RTD is not needed for all applications. Mutations that completely prevent readthrough still allow virion uptake into the hemolymph (Chay, et al. [1996] supra) but absence of the RTD has been shown to decrease the half-life of luteovirus virions in the hemolymph (van den Heuvel, et al. [1997] supra). In the case where whole virions are needed for transport into hemolymph, the CP stop codon is necessary and AaIT is expressed via readthrough, because 100% readthrough prevents virion assembly (Mohan, B. R. [1995] supra). In cases where only a small peptide within the CP is needed for recognition by a hindgut epithelial receptor and subsequent endocytosis into the hemocoel, unnecessary sequences in the CP can be deleted.

Expression of all constructs is monitored by our standard replication assay in protoplasts using northern blot hybridization to detect viral genomic and subgenomic RNAs (Mohan, B. R. [1995] supra; Rasochova, L. et al. [1996] *Molecular Plant-Microbe Interactions* 9:646-650), and western blots to detect CP and CP-RTD as well as ELISA to measure virion accumulation (Brown, C. M. et al. [1996] supra). Aphid toxicity is determined by feeding aphids on extracts of protoplasts, as previously described.

B. Baculovirus Expression System

For measuring the dose response of the CP-RTD-AaIT fusion proteins, aphids are fed on purified recombinant fusion proteins produced in a baculovirus expression system. The various CP-RTD-AaIT fusions described above (FIG. 4) are expressed from DNA coding only for those ORFs (CP, RTD and AaIT) rather than a full replicating BYDV genome. It is preferred to use *Autographa californica* multicapsid nucleopolyhedrovirus (AcMNPV) and standard techniques (O'Reilly, D. R. et al. [1992] *Baculovirus Expression Vectors: A Laboratory Manual*, W. H. Freeman and Company, New York) that are known in the art. The fusion protein sequences are inserted into the Bgl II cloning site of pAcMP1 (Hill-Perkins, M. S. et al. [1990] *J. Gen. Virol.* 71:971-976). Insect cells (*Spodoptera frugiperda*; Sf21: (Vaughn, J. L. et al. [1977] *In Vitro* 13:213-217)) are cotransfected with each recombinant transfer vector and linearized DNA of the virus AcUW1-PH that contains the lacZ gene (Weyer, U. et al. [1990] *J. Gen. Virol.* 71:1525-1534; Kitts, P. et al. [1993] *Biotechniques* 14:810-817). The resulting recombinant viruses express each fusion protein under control of the strong baculovirus late promoter p6.9 (Bonning, B. C. et al. [1994] *J. Gen. Virol.* 75:1551-1556). Recombinant viruses (identified by the absence of β-galactosidase activity in the presence of the substrate X-gal), are purified, amplified and used to infect Sf21 cells for production of fusion proteins (O'Reilly et al. [1992] supra).

The method used for purification of the recombinant fusion proteins from insect cell culture depends on whether virus particles are produced in the cells. Luteovirus coat protein genes have been expressed previously in baculovirus systems resulting in formation of virus particles in the nuclei of infected insect cells (Tian, T. et al. [1995] *Virology* 213:204-212; Blanc, S. et al. [1993] *Virology* 197:283-292).

If virus particles are produced in AaIT fusion constructs, they will be purified by modification of a purification technique that is used routinely for purification of BYDV: the baculovirus-infected cells are lysed by sonication and the BYDV particles purified by differential centrifugation followed by sucrose gradient centrifugation (Rasochova, L. et al. [1996] supra). Because the recombinant virus particles are empty, they settle higher in the gradient than normal virions. If particle assembly does not occur in the baculovirus expression system, one can purify the recombinant proteins using classical protein purification techniques. Specifically, one can purify the recombinant proteins using a polyhistidine tag and a Probond nickel column (Invitrogen) with imidazole elution. The techniques of polyHis fusion tagging and nickel column chromatography are well-known in the art. Recombinant proteins are detected in column fractions by ELISA or western blot, using an anti-AaIT antiserum or anti-CP antisera.

2. Bioassay of Fusion Proteins for Paralytic Effects

A. Aphicidal Efficacy of Ingested CP-RTD-AaIT Fusion Proteins

*Rhopalosiphum padi* nymphs (30 per sample) are membrane-fed as previously described on one of the following: (i) virus extracts from protoplasts inoculated with AaIT-expressing PAV6 transcripts described in 1A above; (ii) purified fusion protein from the baculovirus-expression system (1B above); (iii) recombinant AaIT alone; (iv) unmodified BYDV-PAV virions; (v) buffer alone. The feeding samples also contain sucrose as described above. This medium is layered between two stretched sheets of Parafilm in the standard aphid feed assay (Rasochova, L. [1996] supra). Aphids are fed overnight and monitored for mortality while feeding on the membrane. Bioassays are repeated with a second agriculturally important aphid species, *Myzus persicae*. This species is the major vector of several other economically important luteoviruses including potato leaf roll virus, beet western yellows virus, beet mild yellowing virus, and cucurbit aphid-borne yellows virus, as well as viruses in other groups such as soybean mosaic polyvirus.

The feeding studies described above have demonstrated that both of the desired properties of the BYDV-AaIT fusions are functional: (i) delivery into the hemocoel, and (ii) neurotoxicity. These two properties can be measured separately if desired. As mentioned previously, certain fusion constructs can alter one or both of these activities. Direct injection of the fusion proteins (section 2B) reveals whether AaIT is active as a fusion protein, independent of the transport function provided by the virus proteins. Feeding, followed by analysis of proteins in hemolymph (second 2C) can demonstrate transport into the hemocoel as well as providing an indication of stability in the gut and hemolymph. Data from the described studies can be valuable for optimization purposes.

B. Insecticidal Efficacy of Injected CP-RTD-AaIT Fusion Proteins

As a positive control, one can determine the activity of AaIT fused to BYDV proteins by injecting fusion proteins into larvae of the blow fly *Sarcophaga falculata*. This indicator species is particularly sensitive to scorpion toxins and is useful for evaluation of scorpion venom potency (Zlotkin, E. et al. [1971] *Biochimie* 53:1073-1078). Comparison of the amounts of fusion protein required to cause contraction of *S. falculata* larvae with the amounts of unfused, wildtype AaIT required for contraction will indicate the relative toxicity of AaIT fused to BYDV proteins.

To measure aphid toxicity, one preferably injects apterous (wingless) aphids (which are easier to inject because of the softer cuticle), rather than alate (winged) aphids. Drummond capillaries (20 μl) are pulled and broken with fine forceps to produce a point approximately 10 μm in diameter. Each pulled capillary is used for injection of a single aphid to avoid immune reactions to contaminating hemolymph proteins on the capillary. Aphids are immobilized on a microporous filter by suction through a capillary connected to an aspiration system. Injections are conducted using a microinjection apparatus and a dissecting microscope. The volume injected varies according to the applied pressure, which is standardized, and the internal pressure of each aphid, which is variable. Volumes of 10 to 20 nanoliters can be injected without detriment to the aphid (Gildow, F. E. et al. [1993] *Phytopathology* 83:1293-1302).

C. Detection of AaIT in Aphids

In order to measure the amount of recombinant fusion proteins or control proteins (unmodified BYDV-PAV virions) fed to aphids in section 2A transported into the hemocoel of the aphid, hemolymph samples are collected from 5 aphids in each treatment group by removal of a leg from each aphid and collection of hemolymph in a microcapillary tube (Chay, C. A. [1996] supra). Hemolymph samples from aphids within each group are pooled, and proteins examined by SDS PAGE followed by western blotting. Recombinant proteins are detected in the hemolymph by using antisera to AaIT and/or CP. Hemolymph from aphids fed on AaIT alone or on buffer alone and examined using the AaIT antiserum provide negative controls for test treatments. Hemolymph from aphids fed on BYDV and examined with the CP antiserum provide a positive control for test treatments.

The assays described in section 2 indicate: (i) the toxicity of AaIT fused to BYDV structural proteins; (ii) which ingested fusion protein constructs are optimum for toxicity to aphids and which for reducing probing behavior; (iii) which fusion protein constructs have optimum efficiency for transport into the aphid hemocoel. This information indicates the best constructs suitable for use in production of transgenic plants.

Plants can be rendered transgenic by various techniques known in the art. A "transgenic plant" is one which has been genetically modified to contain and express heterologous DNA sequences, either as regulatory RNA molecules or as proteins. A transgenic plant is genetically modified to contain and express at least one heterologous DNA sequence operably linked to and under the regulatory control of transcriptional control sequences which function in plant cells or tissue or in whole plants. As used herein, a transgenic plant also refers to progeny of the initial transgenic plant where those progeny contain and are capable of expressing the heterologous coding sequence under the regulatory control of the plant-expressible transcription control sequences described herein. Seeds containing transgenic embryos are encompassed within this definition.

When plant expression of a heterologous gene or coding sequence of interest is desired, that coding sequence is operably linked in the sense orientation to a suitable promoter and advantageously under the regulatory control of DNA sequences which quantitatively regulate transcription of a downstream sequence in plant cells or tissue or in planta, in the same orientation as the promoter, so that a sense (i.e., functional for translational expression) mRNA is produced. A transcription termination signal, for example, a polyadenlyation signal functional in a plant cell, is advantageously placed downstream of the CP-RTD coding sequence, and a selectable marker which can be expressed in a plant, can be covalently linked to the inducible expression unit so that after this DNA molecule is introduced into a plant cell or tissue, its presence can be selected and plant cells or tissue not so transformed will be killed or prevented from growing. Where constitutive gene expression is desired, suitable plant-expressible promoters include the 35S or 19S promoters of Cauliflower Mosaic Virus, the Nos, ocs or mass promoters of *Agrobacterium tumefaciens* Ti plasmids, and others known to the art. Where tissue specific expression of the plant-expressible insect resistance coding sequence is desired, the skilled artisan will choose from a number of well-known sequences to mediate that form of gene expression. A useful promoter for expression in plant vascular tissue is obtained from sugarcane bacilliform badnavirus. The promoter (ScBV3m) is active in both monocots and dicots (Olzsewski, N. [1997] *Plant Mol. Biol.*). The promoter sequence is given in Table 4 and SEQ ID NO: 3. Environmentally regulated promoters are also well known in the art, and the skilled artisan can choose from well known transcription regulatory sequences to achieve the desired result.

It is understood that nucleic acid sequences other than that of Table 3, will function as coding sequences synonymous with the exemplified CP-RTD coding sequence. Nucleic acid sequences are synonymous if the amino acid sequences encoded by those nucleic acid sequences are the same. The degeneracy of the genetic code is well known to the art; i.e., for many amino acids, there is more than one nucleotide triplet which serves as the codon for the amino acid; for expression in plant cells or tissue it is desired that codon usage reflect that of plant genes and that CpG dinucleotides be kept low in frequency in the coding sequence. It is also well known in the biological arts that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Vol. 5, Suppl. 3, pp. 345-352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

A plant-expressible transcription and translation regulatory sequence can be operably linked to any promoter sequence functional in plants as understood by the skilled artisan; where a regulatory element is to be coupled to a promoter, generally a truncated (or minimal) promoter is used, for example, the truncated 35S promoter of Cauliflower Mosaic Virus, (CaMV). Truncated versions of other constitutive promoters can also be used to provide CAAT and TATA-homologous regions; such promoter sequences can be derived from those of *A. tumefaciens* T-DNA genes such as Nos, ocs and mas and plant virus genes such as the CaMV 19S gene. It will be understood that the goals of a skilled artisan will determine the choice of particular transcriptional (and translational) regulatory sequences.

A minimal promoter contains the DNA sequence signals necessary for RNA polymerase binding and initiation of transcription. For RNA polymerase II promoters the promoter is identified by a TATA-homologous sequence motif about 20 to 50 bp upstream of the transcription start site and a CAAT-homologous sequence motif about 50 to 120 bp upstream of the transcription start site. By convention, the skilled artisan often numbers the nucleotides upstream of the transcription start with increasingly large numbers extending upstream of (in the 5' direction) from the start site. Generally, transcription directed by a minimal promoter is low and does not respond either positively or negatively to environmental or developmental signals in plant tissue. An exemplary minimal promoter suitable for use in plants is the truncated CaMV 35S promoter, which contains the regions from −90 to +8 of the 35S gene. Where a minimal promoter is used, it is desired that for high levels of gene expression, transcription regulatory sequences which upregulate the levels of gene expression be operably linked thereto. Such quantitative regulatory sequences are exemplified by transcription enhancing regulatory sequences such as enhancers.

Operably linking transcription and translation regulatory sequences upstream of a promoter functional in a plant cell allows the expression of the CP-RTD-toxin fusion coding sequence operably fused just downstream of the promoter, and the skilled artisan understands spacing requirements and ribosome binding site requirements for translational expression of the coding sequence.

Additionally, or alternatively, expression of the regulated construct can be induced, for example, by treating the transgenic plant or tissue with an inducer suitable for regulating expression of the plant-expressible insect resistance coding sequences of the present invention. The expression of the CP-RTD-toxin fusion coding sequence can also be regulated by tissue specific transcription regulatory sequences. In particular, the sugarcane bacilliform badnavirus promoter (ScBV3m) Table 4, is useful for directing expression of a transgene in phloem tissues of both monocots and dicots.

A transgenic plant can be produced by any means known to the art, including but not limited to *Agrobacterium tumefaciens*-mediated DNA transfer, preferably with a disarmed T-DNA vector, electroporation, direct DNA transfer selection and regeneration (see Davey et al. [1989] *Plant Mol. Biol.* 13:275; Walden and Schell [1990] *Eur. J. Biochem.* 192:563; Joersbo and Burnstedt [1991] *Physiol. Plant.* 81:256; Potrykus [1991] *Annu. Rev. Plant Physiol. Plant Mol. Biol.* 42:205; Gasser and Fraley [1989] *Sci.* 244:1293; Leemans [1993] *Bio/Technology.* 11:522; Beck et al. [1993] *Bio/Technology.* 11:1524; Koziel et al. [1993] *Bio/Technology.* 11:194; Vasil et al. [1993] *Bio/Technology.* 11:1533). Techniques are well known to the art for the introduction of DNA into monocots as well as dicots, as are the techniques for culturing such plant tissues and regenerating those tissues. Monocots which have been successfully transformed and regenerated include wheat, corn, rye, rice, oat, barley and asparagus. For efficient regeneration of transgenic plants, it is desired that the plant tissue used in the transformation possess a high capacity to produce shoots. For example, Aspen stem sections have good regeneration capacity. (Devillard, C. III et al. [1992] *C.R. Acad. Sci. Ser. VIE* 314:291-298K; Nilsson et al. [1992] *Transgenic Research* 1:209-220; Tsai et al. [1994] *Plant Cell Rep.* 14:94-97) Poplars have been successfully transformed (Wilde et al. [1992] *Plant Physiol.* 98:114-120).

Techniques for introducing and selecting for the presence of heterologous DNA in plant tissue are well known. For example, *A. tumefaciens*-mediated DNA transfer into plant tissue, followed by selection and growth in vitro and subsequent regeneration of the transformed plant tissue to a plant is well known for a variety of plants.

Other techniques for genetically engineering plant tissue to contain an expression cassette comprising a promoter and associated transcription regulatory sequences fused to the insect resistance coding sequence and optionally containing

TABLE 4

| | |
|---|---|
| C TGCAGGAAGT | (SEQ ID NO: 3) |
| TGAAGACAAA AGAAGGTCTT AAATCCTGGC TAGCAACACT GAACTATGCC | |
| AGAAACCACA TCAAAGATAT GGGCAAGCTT CTTGGCCCAT TATATCCAAA | |
| GACCTCAGAG AAAGGTGAGC GAAGGCTCAA TTCAGAAGAT TGGAAGCTGA | |
| TCAATAGGAT CAAGACAATG GTGAGAACGC TTCCAAATCT CACTATTCCA | |
| CCAGAAGATG CATACATTAT CATTGAAACA GATGCATGTG CAACTGGATG | |
| GGGAGCAGTA TGCAAGTGGA AGAAAAACAA GGCAGACCCA AGAAATACAG | |
| AGCAAATCTG TAGGTATGCC AGTGGAAAAT TTGATAAGCC AAAAGGAACC | |
| TGTGATGCAG AAATCTATGG GGTTATGAAT GGCTTAGAAA AGATGAGATT | |
| GTTCTACTTG GACAAAAGAG AGATCACAGT CAGAACTGAC AGTAGTGCAA | |
| TCGAAAGGTT CTACAACAAG AGTGCTGAAC ACAAGCCTTC TGAGATCAGA | |
| TGGATCAGGT TCATGGACTA CATCACTGGT GCAGGACCAG AGATAGTCAT | |
| TGAACACATA AAAGGGAAGA GCAATGGTTT AGCTGACATC TTGTCCAGGC | |
| TCAAAGCCAA ATTAGCTCAG AATGAACCAA CGGAAGAGAT GATCCTGCTT | |
| ACACAAGCCA TAAGGGAAGT AATTCCTTAT CCAGATCATC CATACACTGA | |
| GCAACTCAGA GAATGGGGAA ACAAAATTCT GGATCC | | a transcription termination region are to be integrated into the plant cell genome by electroporation, co-cultivation, microinjection, particle bombardment and other techniques known to the art. The insect resistance plant expression cassette further contains a marker allowing selection of the expression cassette in the plant cell, e.g., genes carrying resistance to an antibiotic such as kanamycin, hygromycin, gentamicin, or bleomycin. The marker allows for selection of successfully transformed plant cells growing in the medium containing certain antibiotics because they will carry the expression cassette with resistance gene to the antibiotic.

It will be understood by those skilled in the art, that the activity of fusion constructs can be optimized to achieve desired levels of transfer into the hemocoel and of toxin dose. In addition, promoter activity in transgenic plants can be varied using techniques and promoters known in the art, in order to achieve levels of expression optimal for the desired level of aphid control. Such modifications, optimizations and constructs are within the scope of the invention.

We claim:

1. A fusion protein consisting essentially of a first polypeptide segment, said first segment consisting essentially of a luteovirus coat protein or portion thereof necessary for transport of the luteovirus from the gut to the hemocoel of an insect, and a second polypeptide segment, said second segment being a peptide toxic to an insect after transfer to the hemocoel of the insect.

2. A fusion protein according to claim 1, wherein the luteovirus is barley yellow dwarf virus.

3. A fusion protein according to claim 1, wherein the transport peptide is a component of the virus coat.

4. A fusion protein according to claim 1, wherein, the transport protein includes a luteovirus coat protein and at least a portion of the readthrough domain.

5. A fusion protein according to claim 4, wherein the luteovirus is barley yellow dwarf virus.

6. A fusion protein according to claim 1, wherein the insect-toxic peptide is selected from the group TxP-1 of *Pyemotes tritici*, AaIT of *Androctonus australis*, LqhIT1, LghIT2, LghITT3 and Lghαlt of *Leiurus quinquestriatus hebraeus*, AsII of *Anemonia sulcata*, ShI of *Stichadactyla helianthus*, μ-Aga-IV of *Agelenopsis sulcata*, TalTX-1 of *Tegenaria agrestis*, and DTX9.2 of *Diguetia canities*.

7. A fusion protein according to claim 1, wherein the toxin is toxic to insects of the order *Homoptera*.

8. A fusion protein according to claim 1, wherein the toxin is toxic to aphids.

9. A fusion protein according to claim 1, wherein the toxin is toxic to whitefly.

10. A fusion protein according to claim 1, wherein the insect-toxic peptide is AaIT of *Androctonus australis*.

11. A fusion protein according to claim 4, wherein the insect-toxic peptide is AaIT of *Androctonus australis*.

12. A fusion protein according to claim 1 having the amino acid sequence of SEQ ID NO:7.

13. A method of controlling an insect comprising delivering to the insect an effective amount of a fusion protein consisting essentially of a first polypeptide segment, said first segment consisting essentially of a luteovirus coat protein or portion thereof necessary for transport of the luteovirus from the gut to the hemocoel of an insect and a second polypeptide segment, said second segment being a peptide toxic to an insect after transfer to the hemocoel of the insect.

14. The method of claim 13, wherein the insect is a member of the order *Homoptera*.

15. A method according to claim 13, wherein the insect is an aphid.

16. A method according to claim 13, wherein the insect is a whitefly.

* * * * *

SEQUENCE LISTING

<160> NUMBER OF SEQ ID NOS: 7

<210> SEQ ID NO 1
<211> LENGTH: 1956
<212> TYPE: DNA
<213> ORGANISM: Barley yellow dwarf virus

<400> SEQUENCE: 1

```
atgaattcag taggtcgtag aggacctaga cgcgcaaatc aaaatggcac aagaaggagg      60
cgccgtagaa cagttcggcc agtggttgtg gtccaaccca atcgagcagg acccagacga     120
cgaaatggtc gacgcaaggg aagaggaggg gcaaattttg tatttagacc aacaggcggg     180
actgaggtat tcgtattctc agttgacaac cttaaagcca actcctccgg ggcaatcaaa     240
ttcggcccca gtctatcgca atgcccagcg cttttcagacg gaatactcaa gtcctaccat     300
cgttacaaga tcacaagtat ccgagttgag tttaagtcac acgcgtccgc caatacggca     360
ggcgctatct ttattgagct cgacaccgcg tgcaagcaat cagccctggg tagctacatt     420
aattccttca ccatcagcaa gaccgcctcc aagaccttcc ggtcagaggc aattaatggg     480
aaggaattcc aggaatcaac gatagaccaa ttttggatgc tctacaaggc caatggaact     540
accactgaca cggcaggaca atttatcatt acgatgagtg tcagtttgat gacggccaaa     600
taggtagact cctcaacacc ggaaccaaaa cctgcaccgg aaccaacacc aaccccccag     660
ccaacgccgg ctccacagcc cacacctgaa ccaactcctg cacctgtccc caaaagattc     720
ttcgagtata tcggaactcc taccggtaca atctcgacta gagagaacac tgacagtata     780
tctgtcagca agctcggtgg acagtcgatg cagtacattg agaatgagaa atgtgaaacg     840
aaagtcatcg attcctttg gagcactaac aacaacgttt ctgcgcaagc agctttcgtt     900
tatccagtgc cagagggatc atacagcgtt aacatttcgt gcgaaggctt ccagtcagtt     960
gaccacatcg gtggcaacga ggacggctat tggattggtt taattgccta ctccaattcg    1020
tctggcgata attgggggagt tggcaattac aaagggtgca gttttaagaa tttcttggca    1080
accaacactt ggagaccagg ccacaaagat ctcaagttga ctgattgcca gttcacagat    1140
ggacaaatag ttgaaaggga cgccgtgatg tctttccacg tagaagcaac aggcaaggat    1200
gccagcttct acctcatggc tcccaaaaca atgaaaactg acaaatacaa ctatgttgtc    1260
tcatatggag ggtacacaaa caagcgaatg gaattcggta ccatatctgt gacatgtgat    1320
gaatccgatg ttgaggcaga acgaataaca aggcacgctg aaacgcccat acgttctaaa    1380
catattcttg tttctgagcg gtatgcggaa ccattgccca ccatagtcaa ccaaggcttg    1440
tgtgatgtga aaactcccga gcaagaacaa acactggtgg atgaagatga cagacaaact    1500
gtttctactg aatctgatat agcactcctg gagtatgagg ctgcaacagc tgagattccg    1560
gatgctgaag aggacgttttt gccctccaag gaacagttgt cttcaaaacc aatggatacg    1620
```

-continued

```
tctggcaata taataccaaa acccaaggaa cctgaagtac ttgggacata ccaaggacag    1680
aacatttatc ctgaagacgt acctccaatg gcgcggcaga aattgagaga agccgcgaat    1740
gcgccttcca cgctactcta tgaaagaaga accccaaaga agagtggcaa ctttttatcc    1800
agacttgtag aagcgaatag gtcccctact actcccactg ccccatccgt gtcaactact    1860
tcaaacatga caagggagca gctccgggag tacactagga ttagaaattc cagcggaatc    1920
acagcagcaa aggcgtacaa ggcgcaattc cagtga                              1956
```

<210> SEQ ID NO 2
<211> LENGTH: 651
<212> TYPE: PRT
<213> ORGANISM: Barley yellow dwarf virus
<220> FEATURE:
<221> NAME/KEY: UNSURE
<222> LOCATION: (201)
<223> OTHER INFORMATION: The protein shown in this sequence is the product of readthrough translation through an amber codon in SEQ ID NO:1

<400> SEQUENCE: 2

```
Met Asn Ser Val Gly Arg Arg Gly Pro Arg Arg Ala Asn Gln Asn Gly
 1               5                  10                  15

Thr Arg Arg Arg Arg Arg Thr Val Arg Pro Val Val Val Gln
                20                  25                  30

Pro Asn Arg Ala Gly Pro Arg Arg Asn Gly Arg Arg Lys Gly Arg
             35                  40                  45

Gly Gly Ala Asn Phe Val Phe Arg Pro Thr Gly Gly Thr Glu Val Phe
 50                  55                  60

Val Phe Ser Val Asp Asn Leu Lys Ala Asn Ser Ser Gly Ala Ile Lys
 65                  70                  75                  80

Phe Gly Pro Ser Leu Ser Gln Cys Pro Ala Leu Ser Asp Gly Ile Leu
                 85                  90                  95

Lys Ser Tyr His Arg Tyr Lys Ile Thr Ser Ile Arg Val Glu Phe Lys
                100                 105                 110

Ser His Ala Ser Ala Asn Thr Ala Gly Ala Ile Phe Ile Glu Leu Asp
             115                 120                 125

Thr Ala Cys Lys Gln Ser Ala Leu Gly Ser Tyr Ile Asn Ser Phe Thr
130                 135                 140

Ile Ser Lys Thr Ala Ser Lys Thr Phe Arg Ser Glu Ala Ile Asn Gly
145                 150                 155                 160

Lys Glu Phe Gln Glu Ser Thr Ile Asp Gln Phe Trp Met Leu Tyr Lys
                165                 170                 175

Ala Asn Gly Thr Thr Thr Asp Thr Ala Gly Gln Phe Ile Ile Thr Met
             180                 185                 190

Ser Val Ser Leu Met Thr Ala Lys Xaa Val Asp Ser Ser Thr Pro Glu
             195                 200                 205

Pro Lys Pro Ala Pro Glu Pro Thr Pro Thr Pro Gln Pro Thr Pro Ala
210                 215                 220

Pro Gln Pro Thr Pro Glu Pro Thr Pro Ala Pro Val Pro Lys Arg Phe
225                 230                 235                 240

Phe Glu Tyr Ile Gly Thr Pro Thr Gly Thr Ile Ser Thr Arg Glu Asn
                245                 250                 255

Thr Asp Ser Ile Ser Val Ser Lys Leu Gly Gly Gln Ser Met Gln Tyr
             260                 265                 270

Ile Glu Asn Glu Lys Cys Glu Thr Lys Val Ile Asp Ser Phe Trp Ser
```

```
                275                 280                 285
Thr Asn Asn Val Ser Ala Gln Ala Ala Phe Val Tyr Pro Val Pro
    290                 295                 300
Glu Gly Ser Tyr Ser Val Asn Ile Ser Cys Glu Gly Phe Gln Ser Val
305                 310                 315                 320
Asp His Ile Gly Gly Asn Glu Asp Gly Tyr Trp Ile Gly Leu Ile Ala
                325                 330                 335
Tyr Ser Asn Ser Ser Gly Asp Asn Trp Gly Val Gly Asn Tyr Lys Gly
                340                 345                 350
Cys Ser Phe Lys Asn Phe Leu Ala Thr Asn Thr Trp Arg Pro Gly His
    355                 360                 365
Lys Asp Leu Lys Leu Thr Asp Cys Gln Phe Thr Asp Gly Gln Ile Val
    370                 375                 380
Glu Arg Asp Ala Val Met Ser Phe His Val Glu Ala Thr Gly Lys Asp
385                 390                 395                 400
Ala Ser Phe Tyr Leu Met Ala Pro Lys Thr Met Lys Thr Asp Lys Tyr
                405                 410                 415
Asn Tyr Val Val Ser Tyr Gly Gly Tyr Thr Asn Lys Arg Met Glu Phe
            420                 425                 430
Gly Thr Ile Ser Val Thr Cys Asp Glu Ser Asp Val Glu Ala Glu Arg
                435                 440                 445
Ile Thr Arg His Ala Glu Thr Pro Ile Arg Ser Lys His Ile Leu Val
    450                 455                 460
Ser Glu Arg Tyr Ala Glu Pro Leu Pro Thr Ile Val Asn Gln Gly Leu
465                 470                 475                 480
Cys Asp Val Lys Thr Pro Glu Gln Glu Gln Thr Leu Val Asp Glu Asp
                485                 490                 495
Asp Arg Gln Thr Val Ser Thr Glu Ser Asp Ile Ala Leu Leu Glu Tyr
                500                 505                 510
Glu Ala Ala Thr Ala Glu Ile Pro Asp Ala Glu Asp Val Leu Pro
            515                 520                 525
Ser Lys Glu Gln Leu Ser Ser Lys Pro Met Asp Thr Ser Gly Asn Ile
530                 535                 540
Ile Pro Lys Pro Lys Glu Pro Glu Val Leu Gly Thr Tyr Gln Gly Gln
545                 550                 555                 560
Asn Ile Tyr Pro Glu Asp Val Pro Pro Met Ala Arg Gln Lys Leu Arg
                565                 570                 575
Glu Ala Ala Asn Ala Pro Ser Thr Leu Leu Tyr Glu Arg Arg Thr Pro
            580                 585                 590
Lys Lys Ser Gly Asn Phe Leu Ser Arg Leu Val Glu Ala Asn Arg Ser
            595                 600                 605
Pro Thr Thr Pro Thr Ala Pro Ser Val Ser Thr Ser Asn Met Thr
    610                 615                 620
Arg Glu Gln Leu Arg Glu Tyr Thr Arg Ile Arg Asn Ser Ser Gly Ile
625                 630                 635                 640
Thr Ala Ala Lys Ala Tyr Lys Ala Gln Phe Gln
                645                 650

<210> SEQ ID NO 3
<211> LENGTH: 747
<212> TYPE: DNA
<213> ORGANISM: Sugarcane bacilliform virus

<400> SEQUENCE: 3
```

-continued

```
ctgcaggaag ttgaagacaa aagaaggtct taaatcctgg ctagcaacac tgaactatgc      60
cagaaaccac atcaaagata tgggcaagct tcttggccca ttatatccaa agacctcaga     120
gaaaggtgag cgaaggctca attcagaaga ttggaagctg atcaatagga tcaagacaat     180
ggtgagaacg cttccaaatc tcactattcc accagaagat gcatacatta tcattgaaac     240
agatgcatgt gcaactggat ggggagcagt atgcaagtgg aagaaaaaca aggcagaccc     300
aagaaataca gagcaaatct gtaggtatgc cagtggaaaa tttgataagc caaaggaac     360 ctgtgatgca gaaatctatg ggttatgaa tggcttagaa agatgagat tgttctactt       420 ggacaaaaga gagatcacag tcagaactga cagtagtgca atcgaaaggt tctacaacaa     480
gagtgctgaa cacaagcctt ctgagatcag atggatcagg ttcatggact acatcactgg     540
tgcaggacca gagatagtca ttgaacacat aaaaggaag agcaatggtt tagctgacat       600
cttgtccagg ctcaaagcca aattagctca gaatgaacca acggaagaga tgatcctgct     660
tacacaagcc ataagggaag taattcctta tccagatcat ccatacactg agcaactcag     720
agaatgggga acaaaattc tggatcc                                          747
```

<210> SEQ ID NO 4
<211> LENGTH: 2175
<212> TYPE: DNA
<213> ORGANISM: Artificial Sequence
<220> FEATURE:
<223> OTHER INFORMATION: Description of Artificial Sequence: fusion of
      barley yellow dwarf virus coat protein and
      Androctonus australis toxin and readthrough region
      after virus coat.

<400> SEQUENCE: 4

```
atgaattcag taggtcgtag aggacctaga cgcgcaaatc aaaatggcac aagaaggagg      60
cgccgtagaa cagttcggcc agtggttgtg gtccaaccca atcgagcagg acccagacga     120
cgaaatggtc gacgcaaggg aagaggaggg gcaaattttg tatttagacc aacaggcggg     180
actgaggtat tcgtattctc agttgacaac cttaaagcca actcctccgg ggcaatcaaa     240
ttcggcccca gtctatcgca atgcccagcg cttttcagacg gaatactcaa gtcctaccat     300
cgttacaaga tcacaagtat ccgagttgag tttaagtcac acgcgtccgc caatacggca     360
ggcgctatct ttattgagct cgacaccgcg tgcaagcaat cagccctggg tagctacatt     420
aattccttca ccatcagcaa gaccgcctcc aagaccttcc ggtcagaggc aattaatggg     480
aaggaattcc aggaatcaac gatagaccaa ttttggatgc tctacaaggc caatggaact     540
accactgaca cggcaggaca atttatcatt cgatgagtg tcagtttgat gacggccaaa      600
taggtagact cctcaacacc ggaaccaaaa cctgcaccgg aaccaacacc aacccccag      660 ccaacgccgg ctccacagcc cacacctgaa ccaactcctg cacctgtccc caaaagattc     720
ttcgagtata tcggaactcc taccggtaca atctcgacta gagagaacac tgacagtata     780
tctgtcagca agctcggtgg acagtcgatg cagtacattg agaatgagaa atgtgaaacg     840
aaagtcatcg attccttttg gagcactaac aacaacgttt ctgcgcaagc agctttcgtt     900
tatccagtgc cagagggatc atacagcgtt gttaacaaaa aaacggcta cgctgttgac      960 tcttctggca agctccgga atgcctgctg tctaactact gcaacaacca gtgcactaaa     1020
gttcattacg ctgacaaagg ctactgctgc ctgctgtctt gctactgctt cggcctgaac     1080
gacgacaaaa aagttctgga atctctgac actcgtaaat cttactgcga cactactatc     1140
atcaacgtta acatttcgtg cgaaggcttc agtcagttg accacatcgg tggcaacgag     1200
```

```
gacggctatt ggattggttt aattgcctac tccaattcgt ctggcgataa ttggggagtt    1260
ggcaattaca aagggtgcag ttttaagaat ttcttggcaa ccaacacttg agaccaggc    1320 cacaaagatc tcaagttgac tgattgccag ttcacagatg gacaaatagt tgaagggac    1380 gccgtgatgt ctttccacgt agaagcaaca ggcaaggatg ccagcttcta cctcatggct    1440
cccaaaacaa tgaaaactga caaatacaac tatgttgtct catatggagg tacacaaac    1500 aagcgaatgg aattcggtac catatctgtg acatgtgatg aatccgatgt tgaggcagaa    1560
cgaataacaa ggcacgctga aacgcccata cgttctaaac atattcttgt ttctgagcgg    1620
tatgcggaac cattgcccac catagtcaac caaggcttgt gtgatgtgaa aactcccgag    1680
caagaacaaa cactggtgga tgaagatgac agacaaactg tttctactga atctgatata    1740
gcactcctgg agtatgaggc tgcaacagct gagattccgg atgctgaaga ggacgttttg    1800
ccctccaagg aacagttgtc ttcaaaacca atggatacgt ctggcaatat aataccaaaa    1860
cccaaggaac tgaagtact  tgggacatac caaggacaga acatttatcc tgaagacgta    1920
cctccaatgg cgcggcagaa attgagagaa gccgcgaatg cgccttccac gctactctat    1980
gaaagaagaa cccaaagaa gagtggcaac tttttatcca gacttgtaga agcgaatagg    2040 tccccctacta ctcccactgc cccatccgtg tcaactactt caaacatgac aagggagcag    2100
ctccgggagt acactaggat tagaaattcc agcggaatca cagcagcaaa ggcgtacaag    2160
gcgcaattcc agtga                                                    2175
```

<210> SEQ ID NO 5
<211> LENGTH: 724
<212> TYPE: PRT
<213> ORGANISM: Artificial Sequence
<220> FEATURE:
<223> OTHER INFORMATION: Description of Artificial Sequence:fusion of
      barley yellow dwarf virus-Androctonus australus
      toxin-BYDV readthrough domain.
<220> FEATURE:
<221> NAME/KEY: UNSURE
<222> LOCATION: (1)..(724)
<223> OTHER INFORMATION: Xaa is a residue which is either absent or
      unknown.

<400> SEQUENCE: 5

```
Met Asn Ser Val Gly Arg Arg Gly Pro Arg Ala Asn Gln Asn Gly
  1               5                  10                  15

Thr Arg Arg Arg Arg Arg Thr Val Arg Pro Val Val Val Val Gln
                 20                  25                  30

Pro Asn Arg Ala Gly Pro Arg Arg Asn Gly Arg Arg Lys Gly Arg
             35                  40                  45

Gly Gly Ala Asn Phe Val Phe Arg Pro Thr Gly Gly Thr Glu Val Phe
         50                  55                  60

Val Phe Ser Val Asp Asn Leu Lys Ala Asn Ser Ser Gly Ala Ile Lys
 65                  70                  75                  80

Phe Gly Pro Ser Leu Ser Gln Cys Pro Ala Leu Ser Asp Gly Ile Leu
                 85                  90                  95

Lys Ser Tyr His Arg Tyr Lys Ile Thr Ser Ile Arg Val Glu Phe Lys
            100                 105                 110

Ser His Ala Ser Ala Asn Thr Ala Gly Ala Ile Phe Ile Glu Leu Asp
        115                 120                 125

Thr Ala Cys Lys Gln Ser Ala Leu Gly Ser Tyr Ile Asn Ser Phe Thr
    130                 135                 140

Ile Ser Lys Thr Ala Ser Lys Thr Phe Arg Ser Glu Ala Ile Asn Gly
```

```
                145                 150                 155                 160
Lys Glu Phe Gln Glu Ser Thr Ile Asp Gln Phe Trp Met Leu Tyr Lys
                    165                 170                 175
Ala Asn Gly Thr Thr Thr Asp Thr Ala Gly Gln Phe Ile Ile Thr Met
                180                 185                 190
Ser Val Ser Leu Met Thr Ala Lys Xaa Val Asp Ser Ser Thr Pro Glu
                195                 200                 205
Pro Lys Pro Ala Pro Glu Pro Thr Pro Thr Pro Gln Pro Thr Pro Ala
            210                 215                 220
Pro Gln Pro Thr Pro Glu Pro Thr Pro Ala Pro Val Pro Lys Arg Phe
225                 230                 235                 240
Phe Glu Tyr Ile Gly Thr Pro Thr Gly Thr Ile Ser Thr Arg Glu Asn
                    245                 250                 255
Thr Asp Ser Ile Ser Val Ser Lys Leu Gly Gly Gln Ser Met Gln Tyr
                260                 265                 270
Ile Glu Asn Glu Lys Cys Glu Thr Lys Val Ile Asp Ser Phe Trp Ser
                275                 280                 285
Thr Asn Asn Asn Val Ser Ala Gln Ala Ala Phe Val Tyr Pro Val Pro
        290                 295                 300
Glu Gly Ser Tyr Ser Val Val Asn Lys Lys Asn Gly Tyr Ala Val Asp
305                 310                 315                 320
Ser Ser Gly Lys Ala Pro Glu Cys Leu Leu Ser Asn Tyr Cys Asn Asn
                325                 330                 335
Gln Cys Thr Lys Val His Tyr Ala Asp Lys Gly Tyr Cys Cys Leu Leu
                340                 345                 350
Ser Cys Tyr Cys Phe Gly Leu Asn Asp Asp Lys Lys Val Leu Glu Ile
                355                 360                 365
Ser Asp Thr Arg Lys Ser Tyr Cys Asp Thr Thr Ile Asn Val Asn
            370                 375                 380
Ile Ser Cys Glu Gly Phe Gln Ser Val Asp His Ile Gly Gly Asn Glu
385                 390                 395                 400
Asp Gly Tyr Trp Ile Gly Leu Ile Ala Tyr Ser Asn Ser Ser Gly Asp
                    405                 410                 415
Asn Trp Gly Val Gly Asn Tyr Lys Gly Cys Ser Phe Lys Asn Phe Leu
                420                 425                 430
Ala Thr Asn Thr Trp Arg Pro Gly His Lys Asp Leu Lys Leu Thr Asp
            435                 440                 445
Cys Gln Phe Thr Asp Gly Gln Ile Val Glu Arg Asp Ala Val Met Ser
        450                 455                 460
Phe His Val Glu Ala Thr Gly Lys Asp Ala Ser Phe Tyr Leu Met Ala
465                 470                 475                 480
Pro Lys Thr Met Lys Thr Asp Lys Tyr Asn Tyr Val Ser Tyr Gly
                    485                 490                 495
Gly Tyr Thr Asn Lys Arg Met Glu Phe Gly Thr Ile Ser Val Thr Cys
                500                 505                 510
Asp Glu Ser Asp Val Glu Ala Glu Arg Ile Thr Arg His Ala Glu Thr
                515                 520                 525
Pro Ile Arg Ser Lys His Ile Leu Val Ser Glu Arg Tyr Ala Glu Pro
            530                 535                 540
Leu Pro Thr Ile Val Asn Gln Gly Leu Cys Asp Val Lys Thr Pro Glu
545                 550                 555                 560
Gln Glu Gln Thr Leu Val Asp Glu Asp Asp Arg Gln Thr Val Ser Thr
                    565                 570                 575
```

```
Glu Ser Asp Ile Ala Leu Leu Glu Tyr Glu Ala Thr Ala Glu Ile
            580                 585                 590

Pro Asp Ala Glu Glu Asp Val Leu Pro Ser Lys Glu Gln Leu Ser Ser
        595                 600                 605

Lys Pro Met Asp Thr Ser Gly Asn Ile Ile Pro Lys Pro Lys Glu Pro
        610                 615                 620

Glu Val Leu Gly Thr Tyr Gln Gly Gln Asn Ile Tyr Pro Glu Asp Val
625                 630                 635                 640

Pro Pro Met Ala Arg Gln Lys Leu Arg Glu Ala Ala Asn Ala Pro Ser
                645                 650                 655

Thr Leu Leu Tyr Glu Arg Arg Thr Pro Lys Lys Ser Gly Asn Phe Leu
            660                 665                 670

Ser Arg Leu Val Glu Ala Asn Arg Ser Pro Thr Thr Pro Thr Ala Pro
        675                 680                 685

Ser Val Ser Thr Thr Ser Asn Met Thr Arg Glu Gln Leu Arg Glu Tyr
        690                 695                 700

Thr Arg Ile Arg Asn Ser Ser Gly Ile Thr Ala Ala Lys Ala Tyr Lys
705                 710                 715                 720

Ala Gln Phe Gln

<210> SEQ ID NO 6
<211> LENGTH: 2178
<212> TYPE: DNA
<213> ORGANISM: Artificial Sequence
<220> FEATURE:
<223> OTHER INFORMATION: Description of Artificial Sequence:fusion of
      barley yellow dwarf virus coat protein coding
      sequence reading through Androctonus australus
      toxin cds. suqence

<400> SEQUENCE: 6
atgaattcag taggtcgtag aggacctaga cgcgcaaatc aaaatggcac aagaaggagg      60
cgccgtagaa cagttcggcc agtggttgtg gtccaaccca atcgagcagg acccagacga     120
cgaaatggtc gacgcaaggg aagaggaggg gcaaattttg tatttagacc aacaggcggg     180
actgaggtat tcgtattctc agttgacaac cttaaagcca actcctccgg ggcaatcaaa     240
ttcggcccca gtctatcgca atgcccagcg ctttcagacg gaatactcaa gtcctaccat     300
cgttacaaga tcacaagtat ccgagttgag tttaagtcac acgcgtccgc caatacggca     360
ggcgctatct ttattgagct cgacaccgcg tgcaagcaat cagccctggg tagctacatt     420
aattccttca ccatcagcaa gaccgcctcc aagaccttcc ggtcagaggc aattaatggg     480
aaggaattcc aggaatcaac gatagaccaa ttttggatgc tctacaaggc caatggaact     540
accactgaca cggcaggaca atttatcatt acgatgagtg tcagtttgat gacggccaaa     600
taggtagact cctcaacacc ggaaccaaaa cctgcaccgg aaccaacacc aacccccag     660 ccaacgccgg ctccacagcc cacacctgaa ccaactcctg cacctgtccc aaaagattc     720 ttcgagtata tcggaactcc taccggtaca atctcgacta gagagaacac tgacagtata     780
tctgtcagca agctcggtgg acagtcgatg cagtacattg agaatgagaa atgtgaaacg     840
aaagtcatcg attccttttg gagcactaac aacaacgttt ctgcgcaagc agctttcgtt     900
tatccagtgc cagagggatc atacagcgtt gttaacaaaa aaacggcta cgctgttgac     960 tcttctggca agctccgga atgcctgctg tctaactact gcaacaacca gtgcactaaa    1020
gttcattacg ctgacaaagg ctactgctgc ctgctgtctt gctactgctt cggcctgaac    1080
```

-continued

```
gacgacaaaa aagttctgga aatctctgac actcgtaaat cttactgcga cactactatc   1140
atcaactagg ttaacatttc gtgcgaaggc ttccagtcag ttgaccacat cggtggcaac   1200
gaggacggct attggattgg tttaattgcc tactccaatt cgtctggcga taattgggga   1260
gttggcaatt acaaggggtg cagttttaag aatttcttgg caaccaacac ttggagacca   1320
ggccacaaag atctcaagtt gactgattgc cagttcacag atggacaaat agttgaaagg   1380
gacgccgtga tgtctttcca cgtagaagca acaggcaagg atgccagctt ctacctcatg   1440
gctcccaaaa caatgaaaac tgacaaatac aactatgttg tctcatatgg agggtacaca   1500
aacaagcgaa tggaattcgg taccatatct gtgacatgtg atgaatccga tgttgaggca   1560
gaacgaataa caaggcacgc tgaaacgccc atacgttcta acatattct tgtttctgag   1620 cggtatgcgg aaccattgcc caccatagtc aaccaaggct tgtgtgatgt gaaaactccc   1680
gagcaagaac aaacactggt ggatgaagat gacagacaaa ctgtttctac tgaatctgat   1740
atagcactcc tggagtatga ggctgcaaca gctgagattc cggatgctga agaggacgtt   1800
ttgccctcca aggaacagtt gtcttcaaaa ccaatggata cgtctggcaa tataatacca   1860
aaacccaagg aacctgaagt acttgggaca taccaaggac agaacattta tcctgaagac   1920
gtacctccaa tggcgcggca gaaattgaga gaagccgcga atgcgccttc cacgctactc   1980
tatgaaagaa gaaccccaaa gaagagtggc aacttttat ccagacttgt agaagcgaat   2040 aggtcccta ctactcccac tgccccatcc gtgtcaacta cttcaaacat gacaagggag   2100
cagctccggg agtacactag gattagaaat tccagcggaa tcacagcagc aaaggcgtac   2160
aaggcgcaat tccagtga                                                  2178
```

<210> SEQ ID NO 7
<211> LENGTH: 382
<212> TYPE: PRT
<213> ORGANISM: Artificial Sequence
<220> FEATURE:
<223> OTHER INFORMATION: Description of Artificial Sequence:fusion of
      BYDV coat protein, readthrough and Androctonus
      australus toxin.
<220> FEATURE:
<221> NAME/KEY: UNSURE
<222> LOCATION: (1)..(382)
<223> OTHER INFORMATION: Xaa is an unidentified (or absent) residue.

<400> SEQUENCE: 7

```
Met Asn Ser Val Gly Arg Arg Gly Pro Arg Arg Ala Asn Gln Asn Gly
 1               5                  10                  15

Thr Arg Arg Arg Arg Arg Thr Val Arg Pro Val Val Val Val Val Gln
                20                  25                  30

Pro Asn Arg Ala Gly Pro Arg Arg Asn Gly Arg Arg Lys Gly Arg
            35                  40                  45

Gly Gly Ala Asn Phe Val Phe Arg Pro Thr Gly Thr Glu Val Phe
        50                  55                  60

Val Phe Ser Val Asp Asn Leu Lys Ala Asn Ser Ser Gly Ala Ile Lys
 65                  70                  75                  80

Phe Gly Pro Ser Leu Ser Gln Cys Pro Ala Leu Ser Asp Gly Ile Leu
                85                  90                  95

Lys Ser Tyr His Arg Tyr Lys Ile Thr Ser Ile Arg Val Glu Phe Lys
            100                 105                 110

Ser His Ala Ser Ala Asn Thr Ala Gly Ala Ile Phe Ile Glu Leu Asp
        115                 120                 125

Thr Ala Cys Lys Gln Ser Ala Leu Gly Ser Tyr Ile Asn Ser Phe Thr
```

-continued

```
                130                 135                 140
Ile Ser Lys Thr Ala Ser Lys Thr Phe Arg Ser Glu Ala Ile Asn Gly
145                 150                 155                 160

Lys Glu Phe Gln Glu Ser Thr Ile Asp Gln Phe Trp Met Leu Tyr Lys
                165                 170                 175

Ala Asn Gly Thr Thr Thr Asp Thr Ala Gly Gln Phe Ile Ile Thr Met
                180                 185                 190

Ser Val Ser Leu Met Thr Ala Lys Xaa Val Asp Ser Ser Thr Pro Glu
                195                 200                 205

Pro Lys Pro Ala Pro Glu Pro Thr Pro Thr Pro Gln Pro Thr Pro Ala
    210                 215                 220

Pro Gln Pro Thr Pro Glu Pro Thr Pro Ala Pro Val Pro Lys Arg Phe
225                 230                 235                 240

Phe Glu Tyr Ile Gly Thr Pro Thr Gly Thr Ile Ser Thr Arg Glu Asn
                245                 250                 255

Thr Asp Ser Ile Ser Val Ser Lys Leu Gly Gly Gln Ser Met Gln Tyr
                260                 265                 270

Ile Glu Asn Glu Lys Cys Glu Thr Lys Val Ile Asp Ser Phe Trp Ser
                275                 280                 285

Thr Asn Asn Asn Val Ser Ala Gln Ala Ala Phe Val Tyr Pro Val Pro
    290                 295                 300

Glu Gly Ser Tyr Ser Val Val Asn Lys Lys Asn Gly Tyr Ala Val Asp
305                 310                 315                 320

Ser Ser Gly Lys Ala Pro Glu Cys Leu Leu Ser Asn Tyr Cys Asn Asn
                325                 330                 335

Gln Cys Thr Lys Val His Tyr Ala Asp Lys Gly Tyr Cys Cys Leu Leu
                340                 345                 350

Ser Cys Tyr Cys Phe Gly Leu Asn Asp Asp Lys Lys Val Leu Glu Ile
                355                 360                 365

Ser Asp Thr Arg Lys Ser Tyr Cys Asp Thr Thr Ile Ile Asn
    370                 375                 380
```